Figure 1A:
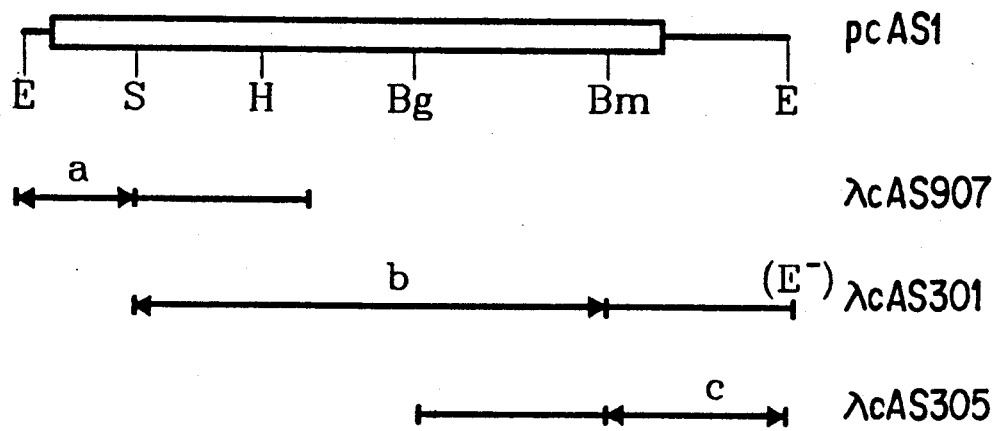

United States Patent [19]

Coruzzi et al.

[11] Patent Number: 5,256,558
[45] Date of Patent: Oct. 26, 1993

[54] GENE ENCODING PLANT ASPARAGINE SYNTHETASE

[75] Inventors: Gloria M. Coruzzi; Fong-Ying Tsai, both of New York, N.Y.

[73] Assignee: The Trustees of Rockefeller University, New York, N.Y.

[21] Appl. No.: 514,816

[22] Filed: Apr. 26, 1990

Related U.S. Application Data

[63] Continuation-in-part of Ser. No. 347,302, May 3, 1989, abandoned.

[51] Int. Cl.⁵ .......................... C12N 5/10; C12N 1/19; C12N 1/21; C12N 15/52
[52] U.S. Cl. .............................. 435/240.1; 435/252.3; 435/320.1; 435/172.3; 435/252.33; 536/23.2; 536/24.1
[58] Field of Search ............... 435/91, 172.3, 240.1, 435/252.3, 252.33, 254, 255, 183, 320.1; 536/27; 935/33, 34, 35

[56] References Cited

U.S. PATENT DOCUMENTS 4,771,002  9/1988  Gelvin ............................. 435/172.3
4,935,363  6/1990  Brown ............................. 435/172.3

OTHER PUBLICATIONS

Wilson (1971), *Botany* (Holt, Rinehart, & Winston, NY), pp. 447-451.
Joy et al. (1983), Plant Physiology, vol. 73, pp. 165-168.
Ray et al. (1984), Gene, vol. 30, pp. 1-9.
Andrulis et al. (1987), Mol. Cell. Biol., vol. 7, pp. 2435-2443.
Lea and Fowden (1975), Proc. R. Soc. Lond. B, vol. 192, pp. 13-26.
Pharmacia, "Cloning Vectors", Pharmacia Catalog, 1989.
Humbert et al. (1980), Journal of Bact., vol. 142, pp. 212-220.
Davidson et al. (1983), Proc. Natl. Acad. Sci., vol. 80, pp. 6897-6901.
Tingey et al., 1987, EMBO Journal 6: 1-9.
Andrulis et al., 1985, J. Biol. Chem. 260(12): 7523-7527.
Herrera-Estrella et al., 1984, Nature 310: 115-120.
Maniatis et al., 1982, "Molecular Cloning," Cold Spring Harbor Library, pp. 295-299.
Rognes, 1975, Phytochen 14:1975.
Ramnefjell & Rognes, 1981, Suppl. Plant Physiol., Abstr. 244.
Huber & Streeter, 1985, Plant Science 42:9-17.
Shelp et al., 1984, Plant science Letters 36:225-230.
Huber & Streeter, 1984, Plant Physiol. 74:605-610.
Loyola-Vargas et al., 1988, J. Plant Physiol. 132:289-293.
Roth & Lark, 1984, Theor. Appl. Genet. 68:421-431.
Hongo et al., 1978, Biochim. Biophys. Acts 522:258-266.
Milman et al., 1979, Biochem. J. 181:51-59.
Markin & Schuster, 1979, Biochem. Biophys. Res. Commun. 88(2):583-588.

(List continued on next page.)

*Primary Examiner*—Richard A. Schwartz
*Assistant Examiner*—Nancy T. Vogel
*Attorney, Agent, or Firm*—Pennie & Edmonds

[57] ABSTRACT

The identification and cloning of the gene(s) for plant asparagine synthetase (AS), an important enzyme involved in the formation of asparagine, a major nitrogen transport compound of higher plants is described. Expression vectors constructed with the AS coding sequence may be utilized to produce plant AS; to engineer herbicide resistant plants, salt/drought tolerant plants or pathogen resistant plants; as a dominant selectable marker; or to select for novel herbicides or compounds useful as agents that synchronize plant cells in culture.

The promoter for plant AS, which directs high levels of gene expression and is induced in an organ specific manner and by darkness, is also described. The AS promoter may be used to direct the expression of heterologous coding sequences in appropriate hosts.

33 Claims, 30 Drawing Sheets

OTHER PUBLICATIONS

Hongo & Sato, 1981, Anal. Biochem. 114:163–166.
Hongo & Sato, 1983, Biochem. Biophys. Acta 742:484–489.
Pfeiffer et al., 1986, J. Biol. Chem. 261 (4):1914–1919.
Pfeiffer et al., 1987, J. Biol. Chem. 262(24):11565–11570.
Arfin et al., 1983, Somatic Cell Genet. 9(5):517–531.
Smith et al., 1984, Cytogen. Cell Genet. 37(1–4) 1985–1986.
Van Heeke & Schuster, 1989, J. Biol. Chem. 264(10), 5503–5509.
Jones, 1978, J. Bacteriol. 134:200–207.
Ramos & Wiame, 1980, Eur. J. Biochem. 118:373–377.
Nakamura, 1981, Nuc. Acids. Res. 9(18):4669–4697.
Scofield & Schuster, 1988, J. Cell Biol. 107:535(a), Abstr. 3023.
Waye et al., 1983, J. Mol. Appl. Genet. 2:69–82.
Cartier et al., 1987, Mol. Cell. Biol. 71(5):1623–1628.
Tsai & Coruzzi, 1990, EMBO J. 9(2):323–332.

AS1 cDNAs

AS2 cDNAs

AS1 genomic clone

AS2 genomic clone

```
  1  CTA CGT GTT GCT TCT TCC ACA CTC TTT GCT CCT AGT TTT TCG TGT CTT GTT TTC TTT ATC CTC TTC TCA TTC TCT TTG GTT CTT   84
  1                                                                                 M  C  G  I  L  A  V  L  E  L  S    25
 85  CAA ATC ATA ATG TGT GGC ATA CTT GCT GTA CTT GGT TGC TCT GAT GAT TCA CAA GCT AAA CGA GTT CGC ATA CTC GAG CTT TCT  168
 26   R  R  L  K  H  R  G  P  D  W  S  G  L  H  Q  H  G  D  N  Y  L  A  H  Q  R  L  A  I                              53
169  CGC AGA TTG AAG CAC CGT GGG CCA GAC TGG AGT GGG CTC CAC CAA CAT GGT GAT AAC TAT TTG GCT CAT CAA AGG TTA GCC ATT  252
 54   V  D  P  A  S  G  D  Q  P  L  F  N  E  D  K  S  I  I  V  T  V  N  G  E  I  Y  N  H                              81
253  GTT GAT CCT GCT TCT GGT GAT CAA CCT CTC TTC AAT GAA GAC AAA TCA ATT ATT GTC ACG GTG AAT GGA GAA ATC TAC AAT CAT  336
 82   E  E  L  R  K  Q  L  P  N  H  K  F  F  T  Q  C  D  C  D  V  I  A  H  L  Y  E  E  H                             109
337  GAA GAG CTC AGA AAA CAA TTG CCC AAT CAC AAG TTT TTT ACA CAA TGT GAC TGT GAT GTT ATT GCA CAC CTG TAC GAG GAA CAT  420
110   G  E  N  F  V  D  M  L  D  G  I  F  S  F  V  L  L  D  T  R  D  N  S  F  I  V  A  R                             137
421  GGA GAA AAT TTT GTG GAT ATG TTA GAC GGT ATA TTT TCG TTT GTT CTG CTG GAT ACT CGT GAC AAC AGT TTC ATA GTT GCG AGG  504
```

FIG.2a

| 138 | D | A | I | G | V | T | S | L | Y | I | G | W | G | L | D | G | S | V | V | I | A | S | E | L | K | G | L | N | 165 |
|---|---|---|---|---|---|---|---|---|---|---|---|---|---|---|---|---|---|---|---|---|---|---|---|---|---|---|---|---|---|
| 505 | GAT | GCT | ATA | GGT | GTT | ACT | TCC | TTG | TAC | ATT | GGT | TGG | GGA | CTA | GAT | GGT | TCT | GTT | GTT | ATT | GCA | TCA | GAA | CTG | AAA | GGA | CTG | AAT | 588 |

| 166 | D | E | C | E | H | F | E | V | F | P | P | G | H | L | Y | S | S | K | E | R | E | F | R | R | W | Y | N | P | 193 |
|---|---|---|---|---|---|---|---|---|---|---|---|---|---|---|---|---|---|---|---|---|---|---|---|---|---|---|---|---|---|
| 589 | GAT | GAA | TGT | GAA | CAT | TTC | GAA | GTT | TTT | CCG | CCC | GGT | CAC | TTA | TAC | TCG | AGC | AAA | GAA | AGA | GAG | TTT | CGT | CGA | TGG | TAT | AAT | CCT | 672 |

| 194 | P | W | F | N | E | A | I | I | P | S | T | P | Y | D | P | L | V | L | R | N | A | F | E | K | A | V | I | K | 221 |
|---|---|---|---|---|---|---|---|---|---|---|---|---|---|---|---|---|---|---|---|---|---|---|---|---|---|---|---|---|---|
| 673 | CCA | TGG | TTC | AAT | GAG | GCT | ATT | ATT | CCG | TCA | ACA | CCT | TAT | GAT | CCT | CTA | GTT | TTG | AGG | AAC | GCG | TTT | GAG | AAG | GCT | GTG | ATA | AAG | 756 |

| 222 | R | L | M | T | D | V | P | F | G | V | L | L | S | G | G | L | D | S | S | L | V | A | S | V | T | A | R | Y | 249 |
|---|---|---|---|---|---|---|---|---|---|---|---|---|---|---|---|---|---|---|---|---|---|---|---|---|---|---|---|---|---|
| 757 | AGG | TTG | ATG | ACC | GAT | GTG | CCT | TTC | GGG | GTT | TTA | CTA | TCG | GGA | GGT | TTG | GAT | TCA | TCG | TTG | GTC | GCG | TCT | GTC | ACT | GCT | AGA | TAC | 840 |

| 250 | L | A | G | T | K | A | A | K | Q | W | G | A | K | L | P | S | F | C | V | G | L | K | G | A | P | D | L | K | 277 |
|---|---|---|---|---|---|---|---|---|---|---|---|---|---|---|---|---|---|---|---|---|---|---|---|---|---|---|---|---|---|
| 841 | CTT | GCT | GGT | ACA | AAA | GCT | GCT | AAG | CAG | TGG | GGA | GCA | AAA | TTG | CCC | TCT | TTC | TGT | GTA | GGC | CTT | AAG | GGC | GCA | CCT | GAC | CTA | AAG | 924 |

FIG.2b

```
278  A   G   K   E   V   A   D   F   L   G   T   V   H   H   E   F   F   T   I   Q   D   G   I   D   A   I   E   305
925  GCT GGA AAG GAG GTA GCA GAT TTC TTA GGA ACT GTC CAT CAT GAA TTT GAG TTT ACT ATC CAG GAC GGT ATA GAT GCA ATT GAA 1008

306  D   V   I   Y   H   T   E   T   Y   D   V   T   T   I   R   A   A   T   P   M   F   L   M   S   R   K   I   K   333
1009 GAT GTC ATC TAT CAC ACA GAA ACA TAT GAT GTT ACT ACG ATA AGG GCT GCA ACA CCT ATG TTT CTG ATG TCT CGT AAG ATC AAA 1092

334  S   S   G   V   K   W   V   I   S   G   E   G   S   D   E   I   F   G   G   Y   L   Y   F   H   K   A   P   N   361
1093 TCA TCC GGA GTC AAA TGG GTG ATT TCT GGA GAA GGA TCT GAT GAG ATC TTT GGA GGG TAT TTG TAT TTC CAT AAG GCG CCA AAC 1176

362  R   E   E   F   H   Q   E   T   C   R   K   I   K   A   L   H   R   Y   D   C   L   R   A   N   K   S   T   Y   389
1177 AGG GAA GAG TTT CAC CAA GAA ACA TGC CGC AAG ATC AAA GCT CTT CAT AGA TAT GAT TGT TTG AGA GCC AAT AAA TCA ACA TAT 1260

390  A   W   G   L   E   A   R   V   P   F   L   D   K   D   F   I   K   V   A   M   D   I   D   P   E   F   K   M   417
1261 GCA TGG GGT CTA GAA GCT AGA GTA CCA TTT TTG GAC AAG GAC TTT ATC AAG GTT GCA ATG GAC ATT GAT CCT GAG TTT AAA ATG 1344
```

FIG. 2c

```
418  I   K   H   D   E   G   R   I   E   K   W   I   L   R   K   A   F   D   D   E   E   N   P   Y   L   P   K   H   445
1345 ATA AAA CAT GAT GAA GGA AGA ATT GAG AAA TGG ATT CTA AGA AAG GCC TTT GAT GAT GAA GAG AAT CCA TAT CTG CCT AAG CAC 1428

446  I   L   Y   R   Q   K   E   Q   F   S   D   G   V   G   Y   G   V   I   D   G   I   K   D   H   A   A   K   H   473
1429 ATT TTA TAT AGG CAG AAG GAA CAA TTC AGT GAT GGA GTT GGA TAT GGC GTT ATA GAT GGC ATC AAG GAC CAT GCT GCA AAA CAT 1512

474  V   T   D   R   M   M   F   N   A   S   H   I   F   P   F   N   T   P   N   T   K   E   A   Y   Y   Y   R   M   501
1513 GTC ACT GAC AGA ATG ATG TTC AAT GCT TCT CAC ATC TTT CCT TTC AAC ACT CCA AAT ACC AAA GAA GCA TAT TAC TAT AGA ATG 1596

502  I   F   E   R   F   F   P   Q   N   S   A   R   L   T   V   P   G   G   P   S   V   A   C   S   T   E   K   A   529
1597 ATC TTT GAA AGG TTT TTC CCT CAG AAC TCG GCA AGG CTT ACA GTT CCT GGA GGA CCT AGT GTT GCA TGC AGC ACA GAG AAA GCT 1680

530  I   E   W   D   A   S   W   S   N   N   L   D   P   S   G   R   A   A   L   G   V   H   V   S   A   Y   E   H   557
1681 ATT GAA TGG GAT GCT TCA TGG TCA AAC AAC CTG GAT CCT TCT GGT AGA GCA GCA CTT GGA GTG CAT GTT TCA GCT TAT GAA CAC 1764
```

FIG.2d

```
 558       Q   I   N   P   V   T   K   G   V   E   P   E   K   I   I   P   K   I   G   V   S   P   L   G   V   A   I   Q    585
1765     CAA ATC AAC CCA GTT ACA AAA GGT GTA GAG CCA GAG AAG ATT ATA CCA AAG ATA GGA GTT TCT CCT CTT GGA GTT GCC ATT CAA   1848

586       T   *                                                                                                            587
1849     ACC TAG TAT GAG ACA TAG CAA GTA TTA CTT GCT TAA AAA ACC AAG ATA TTA TAC TAT TAG TAT TCA ATA AAA AGA ATA ACA         1932

1933     TAA AGG GAA AAT TTG CCT GTT ATG TAT TTT ATC CAG GTA CAG CAT TTG TAT GTA TAA GCC TTT CTA CTT AGC TGT ATT TAT         2016

2017     GTG TTT TGA TGT TGT TGT GTA ATC CAC ATC TTG TCT TTG CTT TTA ATT GAT GTG GTG ATT TGA ACA CTT TCA GAT TGT AAT TTG GCT 2100

2101     TTT TAA GAA GAG TTG TGT ATT ATG TTA AAT TTG AGT GCA AGT TTC ACT ATT TGA ATA CTA CTT ATA AAT ATA TGT CTT TAC ATT     2184

2185     AAA AAA AAA AAA AAA A                                                                                               2200
```

FIG.2e

```
1    TT CCA AAG CCA TTA TTA GTA TTA CAA CTA CAT ACA TAT TTT CTT CTT AGT TTA TTC CAA ATT CTG TCT TTG ATT TCA TTA TCG   83

M   C   G   I   L   A   V   L   G   C   S   D   P   S   R   A   K   R   V   R   V   L     22
1

84   TAT AAA ACA TAA ACA ACA ATG TGT GGT ATA CTT GCT GTT CTT GGT TGT TCT GAT CCT TCT CGA GCC AAG AGA GTT CGT GTG TTG  167

23    E   L   S   R   R   L   K   H   R   G   P   E   W   S   G   L   H   Q   H   G   D   C   Y   L   A   Q   Q   R    50

168  GAA CTT TCA CGC AGA TTG AAG CAC CGA GGC CCT GAA TGG AGT GGG CTC CAC CAA CAT GGT GAT TGT TAT TTG GCA CAA CAA CGG  251

51    L   A   I   V   D   P   A   S   G   D   Q   P   L   F   N   E   D   N   P   S   I   V   T   V   N   G   E   I    78

252  TTA GCC ATA GTT GAT CCT GCT TCT GGT GAT CAA CCT CTC TTC AAT GAA GAC AAT CCG TCA ATT GTC ACG GTA AAC GGA GAG ATT  335

79    Y   N   H   E   D   L   R   K   Q   L   S   N   H   T   F   R   T   G   S   D   C   D   V   I   A   H   L   Y   106

336  TAC AAT CAT GAA GAT CTC AGG AAA CAG TTG TCT AAT CAC ACG TTT AGG ACC GGA AGT GAT TGT GAT GTT ATT GCG CAT TTG TAC  419
```

FIG. 2f

```
107  E   E   Y   G   E   D   F   V   D   M   L   D   G   I   F   S   F   V   P   L   D   T   R   D   N   S   Y   I   134
420  GAG GAA TAT GGA GAA GAC TTT GTG GAT ATG TTG GAT GGT ATA TTT TCG TTT GTT CCA TTG GAT ACT CGT GAC AAC AGT TAT ATT 503

135  V   A   R   D   A   I   G   V   T   S   L   Y   I   G   W   G   L   D   G   S   V   V   I   S   S   E   M   K   162
504  GTG GCT AGA GAT GCG ATT GGT GTA ACT TCT CTA TAC ATT GGT TGG GGA TTA GAT GGT TCG GTT TGG ATT TCG TCG GAA ATG AAA 587

163  G   L   N   D   D   C   E   H   F   E   C   F   P   P   G   H   L   Y   S   S   K   D   S   G   F   R   R   W   190
588  GGT TTG AAC GAT GAT TGT GAA CAT TTC GAG TGT TTT CCA CCT GGT CAT TTG TAT TCG AGC AAA GAT AGT GGC TTT AGA AGA TGG 671

191  Y   N   P   S   W   Y   S   E   A   I   P   S   A   P   Y   D   P   L   A   L   R   H   A   F   E   K   A   V   218
672  TAT AAT CCT TCT TGG TAC TCT GAG GCT ATT CCG TCG GCT CCT TAT GAT CCT CTT GCT TTG AGG CAC GCC TTC GAG AAG GCG GTG 755

219  V   K   R   L   M   T   D   V   P   F   G   V   L   L   S   G   G   L   D   S   S   L   V   A   S   I   T   S   246
756  GTA AAA AGG TTG ATG ACA GAT GTA CCT TTC GGT GTT CTA CTA TCC GGA GGT TTG GAC TCG TCA TTG GTT GCA TCC ATC ACT TCT 839
```

FIG. 2g

```
247  R   Y   L   A   T   T   K   A   A   E   Q   V   G   S   K   L   H   S   F   C   V   G   L   E   G   S   P   D   274
840  CGC TAC CTA GCA ACC ACG AAA GCG GCT GAA CAA TGG GGA TCA AAA CTA CAT TCA TTC TGC GTT GGA CTC GAG GGC TCA CCT GAT  923

275  L   K   A   G   K   E   V   A   D   Y   L   G   T   V   H   H   E   F   T   F   T   V   Q   D   G   I   D   A   302
924  CTT AAG GCT GGA AAA GAA GTT GCA GAT TAT CTC GGA ACC GTT CAT CAT GAG TTT ACT TTT ACT GTT CAG GAT GGT ATA GAT GCA 1007

303  I   E   D   V   I   Y   H   V   E   T   Y   D   V   T   S   I   R   A   S   T   P   M   F   L   M   S   R   K   330
1008 ATT GAG GAT GTT ATA TAC CAT GTT GAA ACA TAT GAT GTT ACT TCA ATT AGA GCA AGC ACG CCT ATG TTT CTC ATG TCG AGG AAG 1091

331  I   K   S   L   G   V   K   W   V   I   S   G   E   G   S   D   E   I   F   G   G   Y   L   Y   F   H   K   A   358
1092 ATT AAA TCA CTT GGT GTC AAA TGG GTG ATC TCC GGT GAA GGA TCC GAT GAG ATC TTT GGC GGA TAT CTG TAC TTT CAC AAG GCA 1175

359  P   N   K   E   E   F   H   E   E   T   C   R   K   I   K   A   L   H   Q   Y   D   C   Q   R   A   N   K   S   386
1176 CCG AAC AAG GAA GAG TTT CAC GAA GAG ACT TGC CGC AAG ATC AAA GCA CTG CAC CAA TAT GAT TGC CAG AGA GCT AAT AAA TCG 1259
```

FIG.2h

```
387   T   Y   A   V   G   L   E   A   R   V   P   F   L   D   K   A   F   I   N   V   A   M   N   I   D   P   E   N   414
1260  ACT TAT GCT TGG GGT TTA GAA GCT AGA GTT CCG TTT CTG GAC AAG GCG TTT ATC AAT GTT GCG ATG AAT ATT GAT CCT GAG AAT  1343

415   K   M   I   K   R   D   E   G   R   I   E   K   Y   I   L   R   K   A   F   D   D   E   E   N   P   Y   L   P   442
1344  AAA ATG ATA AAA CGA GAT GAA GGA CGA ATT GAG AAG TAT ATT TTG AGG AAG GCA TTT GAT GAC GAA GAG AAT CCT TAT CTG CCA  1427

443   K   H   I   L   Y   R   Q   K   E   Q   F   S   D   G   V   G   Y   S   W   I   D   G   L   K   A   H   A   A   470
1428  AAG CAC ATT TTG TAT AGG CAG AAA GAA CAA TTC AGT GAT GGA GTT GGT TAT AGC TGG ATT GAT GGT CTT AAA GCT CAT GCT GCA  1511

471   K   H   V   T   D   K   M   M   L   N   A   G   N   I   F   P   H   N   T   P   N   T   K   E   A   Y   Y   Y   498
1512  AAA CAT GTG ACC GAT AAA ATG ATG CTT AAT GCT GGT AAT ATC TTC CCG CAC AAC ACA CCA AAC ACA AAG GAA GCA TAC TAC TAC  1595

499   R   M   I   F   E   R   F   F   P   Q   N   S   A   R   L   T   V   P   G   G   P   T   V   A   C   S   T   A   526
1596  AGA ATG ATC TTT GAG CGG TTC TTC CCT CAG AAC TCG GCA AGA CTA ACT GTT CCC GGA GGA CCA ACG GTT GCA TGT AGC ACA GCA  1679
```

FIG. 2i

```
527  K   A   V   E   W   D   A   A   W   S   N   N   L   D   P   S   G   R   A   A   L   G   V   H   D   S   A   Y   554
1680 AAA GCT GTT GAG TGG GAT GCT GCT TGG TCA AAC AAC CTC GAT CCT TCT GGT AGA GCA GCA CTC GGA GTT CAT GAT TCA GCT TAT 1763

555  E   N   H   N   K   V   N   K   T   V   E   F   E   K   I   I   P   L   E   A   A   P   V   E   L   A   I   Q   582
1764 GAA AAC CAT AAC AAA GTC AAC AAA ACT GTA GAG TTT GAG AAG ATT ATA CCA CTG GAA GCC GCT CCT GTC GAG CTT GCC ATC CAG 1847

583  G   *   584
1848 GGC TAG TTT CAG CTA TGG CAA GGA ATG ACT GTG CTA GAA GAA TGA AGA TAA TAA TTG AAA ACT TAA CAT ATA TGA AGA ATT TGC 1931

1932 CTT CTG TTT AAT TTT ATC CGG GGC GAA ACA ATG CTA TAT AAT ATA GAT AAA GCT TTA AAT AAA AAA AAA AA 2002
```

FIG.2j

```
AS2      MCGILAVLGCSDPSRAKRVRVLELSRRLKHRGPE---WSGLHQHGDCYLAQQRLAIVDPA
         ::::::::::::: :::::::: :::::::::::   ::::::::: :::  ::::::
AS1      MCGILAVLGCSDDSQAKRVRILELSRRLKHRGPD---WSGLHQHGDNYLAHQRLAIVDPA
         :::: :: :  :    ::    :                    ::   ::   :    :
AShuman  MCGIWALFG-SDDCLS--VQCLS-AMKIAHRGPDAFRFENVNGYTNCCFGFHRLAVVDPL
                   10          20          30         40          50

AS2      SGDQPLFNEDNPSI-VTVNGEIYNHEDLRKQLSNHTFRTGSDCDVIAHLYEEYG-EDFVD
         ::::::::::: :: :::::::::::: ::::::  :::::::::::::::: : ::::
AS1      SGDQPLFNEDKSII-VTVNGEIYNHEELRKQLPNHKFFTQCDCDVIAHLYEEHG-ENFVD
               :    :  :::::::::::                  ::  :::::   :
AShuman  FGMQPIRVKKYPYLWLCYNGEIYNHKKMQQHF-EFEYQTKVDGEIILHLYDKGGIEQTIC
                    60          70         80         90         100

AS2      MLDGIFSFVPLDTRDNSYIVARDAIGVTSLYIGWGLDGSVWISSEMKGLNDDCEHFECFP
         ::::::::::::::::: ::::::::::::::::::::::::: :::::::: :::: :
AS1      MLDGIFSFVLLDTRDNSFIVARDAIGVTSLYIGWGLDGSVWIASELKGLNDECEHFEVFP
         ::::                                        ::  :
AShuman  MLDGVFAFVLLDTANKKVFLGRDTYGVRPLFKAMTEDGFLAVCSEAKGLVTLKHSATPFL
               110         120        130         140         150
```

FIG. 3a

```
AS2      ------------PGHLYSSKDSGFRRWYNPSWYSEA-IPSAPYDPLALRHAFE
              ::::::::::::: :: :::::::: :::::::
AS1      ------------PGHLYSSKEREFRRWYNPPWFNEAIIPSTPYDPLVRNAFE
                       ::     ::
AShuman  ......EVLDLKPNGKVASVEMVKYHHCRDVPLHALYDNVEKLFPGFEIETVKNNLRILFN
                             200
                                      250
AS2      KAVVKRLMTDVPFGVLLSGGLDSSLVASITSRYLATTKAAEQWGSKLHSFCVGLEGSPDL
         ::: :::::::::::::::::::::::: :::::: :::::: ::::::::: :::
AS1      KAVIKRLMTDVPFGVLLSGGLDSSLVASVTARYLAGTKAAKQWGAKLPSFCVGLKGAPDL
         :::  :::       ::::::::: ::    :         :        ::::
AShuman  NAVKKRLMTDRRIGCLLSGGLDSSLVA---ATLLKQLKEAQV-QYPLQTFAIGMEDSPDL
                            250
                                      300
AS2      KAGKEVADYLGTVHHEFTFTVQDGIDAIEDVIYHVETYDVTSIRASTPMFLMSRKIKSLG
         :: ::::: ::::::::::::::::::::::::  :::::::  :::::::::::: :
AS1      KAGKEVADFLGTVHHEFEFTIQDGIDAIEDVIYHTETYDVTTIRAATPMFLMSRKIKSSG
          :: :::::  ::         :::::::  ::::  ::    :::    ::::::
AShuman  LAARKVADHIGSEHYEVLFNSEEGIQALDEVIFSLETYDITTVRASVGMYLISKYIRKNT
                            300
                                     350
```

FIG.3b

```
                350
AS2      VKWVI-SGEGSDEIFGGYLYFHKAPNKEEFHEETCRKIKALHQYDCQRANKSTYAWGLEA
         :::: ::::::::::::::::::::::::::::::: ::::  ::::::::::::::::
AS1      VKWVI-SGEGSDEIFGGYLYFHKAPNREEFHQETCRKIKALHRYDCLRANKSTYAWGLEA
          :  ::::::::: :::::::::  :         :   ::::      :   :::
AShuman  DSVVIFSGEGSDELTQGYIYFHKAPSPEKAEEESERLLRELYLFDVLRADRTTAAHGLEL
                       400

400                                        450
AS2      RVPFLDKAFINVAMNIDPENKMIKRDEGRIEKYILRKAFDDEENPYLPKHILYRQKEQFS
         ::::::::.::::::::::::::::::::::::::::::::::::::::::::::::::
AS1      RVPFLDKDFIKVAMDIDPEFKMIKHDEGRIEKWILRKAFDDEENPYLPKHILYRQKEQFS
         ::::::  :: :   ::  : :: ::    ::    ::         :::: ::::  :
AShuman  RVPFLDHRFFSYYLSLPPEMRIPK--NG-IEKHLLRETF--EDSNLIPKEILWRPKEAFS
                                         450

500
AS2      DG---VGYSWIDGLKAHAAKHVTDKMLMLNAGNIFPHNTPNTKEAYYYRMIFERFFPQNSA
         ::   ::: :::: : :::::::::  :::::  :::::::::::::::::::::::::::
AS1      DG---VGYGWIDGIKDHAAKHVTDRMMFNASHIFPFNTPNTKEAYYYRMIFERFFPQNSA
           :    : ::: : :  : : :  :  :         ::::: : ::::  : ::: :
AShuman  DGITSVKNSWFKILQEYVEHQVDDAMMANAAQKFPNTPKTKEGYYYRQVFERHYPGRAD
                                        500
```

FIG.3c

```
                                                      550
AS2       RLTVPGGPTVACSTAKAVEWDAAWSNNLDPSGRAALGVHDSAYENH-NKVNKTVEFEKII
          ::::: :::::: :: ::::::::::::::::::::: :::::  :: :: :::::
AS1       RLTVPGGPSVACSTEKAIEWDASWSNNLDPSGRAALGVHVSAYEHQINPVTKGVEPEKII
AShuman   WLSHYWMPKWINATDPSARTLTHYKSAVKA
                      550

AS2       P-LEAAPVELAIQG
          :  :  ::: :::
AS1       PKIGVSPLGVAIQT
```

FIG. 3d

AS1

S  E  B  H 1  2  3  4

AS2

S  E  B  H 5  6  7  8

Kb: 23.7, 9.5, 6.6, 4.2, 2.2, 1.9, 1.4

D  L

— AS1
— chloroplast GS 1  2

L  D  L

AS1
chloroplast GS 1  2  3

R/
D  R  FR  L 2.2kb  —AS1

1  2  3  4

FIG.6a
cotyledons
DAY 2 4 6 8 10 12 15 18
 AS1
2.2 kb
 AS2
2.2 kb
1 2 3 4 5 6 7 8
FIG.6b
nodules
R   N
2.2 kb  AS1
2.2 kb  AS2
2.1 kb  beta ATPase
1 2

```
-2376  GGATCCTATC AGTACAAGTC GAACTCGATC ACAAGGTTTA TACGCCATTT GAAGGATCAC
-2316  AAGAGACGGT TACAATATGA TACATTATGG CAGGGAGTTA TAATTATTGA AGAGGCGATT
-2256  GTTAAAAAAT AATTATAAAG GGCGACAGGC GTTATTGATA GGAGAATTTA TGAAGGATAT
-2196  GGAGAGTCGG GAAGGGGGAG AATGAGACCT ATAAATAAGA GGATATTTTG AGGGTAGATA
-2136  GGGGAGAAAA ACACAGAAAC CTCACATAAC AGACACTCCA ACCATTCATT TTAGNCTCTC
-2076  CTTGAACTAG AACAGGGAAA TCAACATTTT AGTGTTTTTT AGCAACAACA GTTCCATTT
-2016  GGTATTTTGA GTATGAATAT TTTGGTGTGT GTTGACTTCG ACCCGGAAGA AGATGAATCC
-1956  ATTAATGAAT CAACCAGGAT ATGGACTCAT GCATTAAGGC ACATGGGAAT GTCCATTATA
-1896  TATGTAGTGG ACCCAAAACA AGGAGGTTCA TCAACTCTAA AGGATTTTGA
-1836  TTATGAGATC CCTTAAATGA CTTCTACTGA AGTTATCTCT ACAACATCAT CAAATAGAAA
-1776  AAGTAGACAA GAAAAAGAT TTACTATCTT CGCCACTGTT CTATCAAGAT CGAGATATTT
-1716  TGTTTGAGGT ATCGAGTCAA ATTCAATCAA GACAACACCT AATGTCAAGT GGTGTTTGAT
-1656  AGAGTCCTTG ATGATTGTTG GTCAAGAAAA ATCTGATGAT GGTGTCTATC GAGAAGCTTT
-1596  ATCAAGCCTT ATCTTGAAGT CAAGTCCCAA ATAAAGTGTT GAATTAAGCA AGGGAGTTTG
```

FIG. 10a

```
-1536  AAGCTTCAAA ATTTGTNAAA AAAAGGAAGT GTGAAAGCTC GTTGAATTGT GTCTTAGTGA

-1476  CTAATGTATT GTAAAGATAT AAGAGTAATT CTCAAATAGT TACCAGGAAA ACTTCATGGA

-1416  AAACTTCTTA CTAATGTGCA AAGGAAAGGT CAGGGTAATG CATGCCCGTG AGACTATTAT

-1356  GCATGTCATT AGAGATTGCA TCGTAGTTAA GAGTTTACGA AATAAATTTA GTACCTATGA

-1296  ATTATGATAA TTAGGGTATT TTTTAGTCTT GAATTATTCA ATGGGTAAAT TTATCTTCAA

-1236  GTCTTTTTCA ATGGTACTA TTCAAGGGAA CTAGCCTACT CTCTTAAGCT ATCATGGCAT

-1176  ATTNTNTNTG CCAAGATAAA AGCCAATTAG ACATAATTTT TTTCTCAAA AACTTACAAT TATTATTAA

-1116  AAAAAAAAAT AGTAATAGTT ACATAATTTT ACATAATTTT TGAAATCAAT ATCAACGAAT TACTCCTTCA TCAATCTCT

-1056  TTTGTCTAGC AAAGGAAACA TGAAATCAAT TTAGAGACTC TAAGAAAATT TATATTAGNT CATTTTTATT

-996   CTTTTCGTTT CTGGGGTATA TTAGAGACTC TGTATTTCTG TTGATCTAAG ATATATTCCA TAATTAAAA

-936   GTAATCTTGA TCGATCTATC TGTATTTCTG CATTCCTTAT TTCTTAGAC GGATTCATTT GTTGTGGTTA

-876   ATGACAAGTA ATTTGACTTT CATTCCTTAT TTCTTAGAC GGATTCATTT GTTGTGGTTA

-816   ATACGATAAT CTTCAACAA AAAACTCGT AATCTAAATT TACTTTTGTT TCTTCTCGAA
```

FIG.10b

```
-756  ATCCAATCCG TCATAAATCA AACATACTAA AAGTGTGAGA TTAGACATAT TTATATTTAT
-696  AAAGAATAAA TCGATCTTGC ATATATTCAC GAATTATTT  AATATAATTT TTAACTCTTA
-636  AATCATCTTA ACCTTTTTTT TTATTGATGT GTGATTATTG TAGAGAAGCT TCATTCTCTT
-576  CTATTATTTC TTAGGCATGC TTTCTAGATT TCCTATAAGA AAAAGAAGA  CAAATTAACT
-516  AAATAAATCG GCACAAGAAA TACTACGGTA GAATTAGTCC ATGGAAACAA AGTCAATCTA
-456  ATGAGAAACT TAAGAATTGG TTTATCAAAA AAAATAGTTA ATAAAGTTCT ACACATTTTA
-396  CCACCTATTT AATCAGTAAT CACTATTATT AATATGTCAA AACGGATACA AGCTGACGCA
-336  GCACTCAAAA ACAAAAGTTA AACAGTTATG GATAAGCCTT TCCACTCTCA TTTATTTAAA
-276  AGAAGCAGCA AACCGCTCAA GCATAAACTA GAATCAAATA AACTAATTAA ATAAATAAAT
-216  AAACCAATAA TGATAAATAA ATGGATTTAG TAAATAACTT GACAAAAACA
-156  TCCCATAGCA AACCACGTCA CAGGACGTAG CAATAGGCGTG GTCCGATTAC GTCACCGGCA
-96   CTACCCGTTC CCGGTAGACA CTTCTTCAAA ACCCCAAACG ACACCGTTTA GCTCCCACCT
-36   TTCGTGTATA AATACGTGTA CGTCGATAGA TATAGTACTT AACACGATCG AATTGAAACC
```

FIG.10c

```
  1 GCCTGCAGGT CGACTCTAGA GGATCTAACA CTTGGATTAA ATTAGGGTTC ACATCGTATG
 61 CCTCGAACAA ATAGAGGTGT AGGTCAGAGG TCCACACATAA GCCATTGGGT CATACAATTA
121 ATTATGTGGG ATTAATTTGA AAATATATTAT GGATCGATTT AATTTTAAAA AATATATGGG
181 AGACTAATTT GCAAAATTTA AAGATTAGT AATAACTAAT TTGAAACTTA CAATGTATAG
241 AGTGAAAGAA ATTTTCCAA ATTTCTTATT TTAAGTGTAA TTTAAAATTC CTTATAACTT
301 GAACAAGTAC TTTATAAAAT TTCATCATTT TAATCAATTT TCTTTATATT CATCCACGCT
361 ATTAACGATC TCATCAAAAT AGCTTGTCCC CCAATTGAGA CTATTATTAT GTATGTTTTA
421 ATTTTTGATT GAAACAAATT TAAATGAATT GAACTTGGAA AATTAATTTT TTAATTTGTT
481 TCTATATAAT AATAAGACAA TTTTTAGTT AGTGTTGAGA TATAAGGAAA TAATCGAATA
```

FIG.12a

```
541  ATAGTAAAAC ATTAACAGA TAAGTAATTT ATAAATGATT TATTTAGAAA AAATAAACCT
601  CAAATAAAAA AATCACAATA GTTTTAAAAT AAAAAATATT TCAATTAATC ATCAAATTAT
661  TGTCGTGTGT ACCGAAAACT ATTGTCCTGA ATTGTACTAA ATAAAAACAT CCATAAATAA
721  TGTTGGCGAT TACCAAAACT AAACATGGAG TACTTATGTT GTGAACACAA ACTAAACTAA
781  AATAAGAAAA ACAATACTAA NNNAAAGTCG ATACCAATAA CGAACCAGGT CTATCCACAT
841  GGCATATTAT AGTTTGTATA AACAATGGGT CCCACATTTT GTGTCATGGA CCATCCAATC
901  GCAAGTAACA ACAGTACATT GAATTTGAAT AATCGAAAAC GACGTCGTTT CTCCGTCAGC
961  ATTTTATGTC TATCGTTCTT TTATGCCTTA TAAATACATG TTCGAGGACG TGTTATTCAT
1021 ACTGAATTGG TTCCAAAGCC ATTATTAGTA TTACAACTAC ATACATATTT TCTTCTTAGT
1081 TTATTCCAAA TTCTGTCTTT GATTCATTA TCGTATAAAC A
```

FIG.12b

```
            -158         -146
     AS1    CATCCCATAGCAA
            ::::: :: :::::
     AS2    CATCCAATCGCAA

-61          -48
     AS1    AAACGACACCGTTT
            :::::::  :::::
     AS2    AAACGACGTCGTTT

-46      -38
     AS1    TCCCACCTT
            ::::::  ::
     AS2    TCCCACATT

-126  -120
     AS1    CAATAGC
            :::: ::
     AS2    CAATCGC

-137      -127
     AS1    ACAGCACGTAG
            ::::  ::  : :
     AS2    ACAGTACATTG

-118     -110
     AS1    TGGTCCGAT
            :::  :: ::
     AS2    TGGACC-AT

-113  -107
     AS1    CGATTAC
            :::::::
     AS2    CGATTAC

-104    -97
     AS1    CACCGGCA
            ::::  :::
     AS2    CACC-GCA
```

FIG.13

GENE ENCODING PLANT ASPARAGINE SYNTHETASE

The invention described herein was supported in whole or in part by a grant from the National Institute of Health, and the United States Department of Energy.

The present application is a continuation in part of application Ser. No. 07/347,302 filed May 3, 1989, now abandoned.

TABLE OF CONTENTS

1. Introduction
2. Background Of The Invention
   2.1. Mammalian, Bacterial And Yeast Asparagine Synthetases
   2.2. Plant Asparagine Synthetase
3. Summary Of The Invention
   3.1. Definitions
4. Description Of The Figures
5. Description Of The Invention
   5.1. Plant Asparagine Synthetase Coding Sequence
   5.2. Expression Of Plant Asparagine Synthetase
      5.2.1. Construction Of Expression Vectors Containing The Plant AS Coding Sequence
      5.2.2. Identification of Transfectants Or Transformants Expressing The Plant AS Gene Product And Isolation Of Plant AS
   5.3. Uses Of Plant Asparagine Synthetase Gene and Gene Products
      5.3.1. Production Of Antibodies That Define And/Or Inhibit Plant AS
      5.3.2. Development Of New Herbicides
      5.3.3. Development Of Herbicide Resistant Plants And Stress Tolerant Plants
      5.3.4. Identification Of Agents That Synchronize Plant Cells In Culture
   5.4. The Plant Asparagine Synthetase Promoter
6. Example: cDNA Cloning Of Plant Asparagine Synthetase
   6.1. Materials and Methods
      6.1.1. Isolation Of Plant AS1 cDNAs
      6.1.2. Synthesis Of Full Length AS1 cDNA
      6.1.3. Isolation Of Plant AS Genomic Clones
      6.1.4. Isolation Of Plant AS2 cDNAs
      6.1.5. DNA And RNA Analyses
   6.2. Results
      6.2.1. Isolation Of Two Classes Of Pea AS cDNA Clones
      6.2.2. pcAS1 And cAS2 Represent Homologous AS mRNAs Which Encode Distinct AS Polypeptides
      6.2.3. AS1 And AS2 Are Encoded By Single Nuclear Genes In The Pea Genome
      6.2.4. Photophobic Accumulation Of AS1 mRNA In Leaves
      6.2.5. Both AS1 and AS2 mRNAs Are Expressed At High Levels During Developmental Contexts Involving Increased Nitrogen Transport
   6.3. Discussion
7. Example: The AS Promoter
   7.1. Dark-Induced Accumulation Of AS mRNA Occurs In All Organs Tested
   7.2. The Dark-Induced Expression Of AS1 Gene Is Not Regulated By Circadian Rhythm
   7.3. The Dark-Induced Expression Of AS Genes In Pea Leaves Is Regulated At The Level Of Transcription
   7.4. The 569 Base Pair Fragment Of The AS1 Promoter Is Sufficient To Drive GUS Expression In Transgenic Plants
   7.5. AS1 And AS2 Genes Contain Conserved Sequence In Their Promoters
8. Deposit Of Microorganisms

1. INTRODUCTION

The present invention relates to the cloning and expression of plant asparagine synthetase, an important enzyme involved in the formation of asparagine, a major nitrogen transport compound of higher plants. Recombinant DNA techniques are used to construct cDNA clones of plant asparagine synthetase. These clones may be used to construct expression vector/host systems that produce plant asparagine synthetase which, in turn, can be used for a variety of purposes including the generation of antibodies that define plant asparagine synthetase. The clones can also be used to overproduce wild type or altered forms of asparagine synthetase in order to engineer herbicide resistant plants, salt/drought tolerant plants, and pathogen resistant plants; as a dominant selectable marker; and/or to select for novel herbicides or compounds useful as agents which synchronize plant cells in culture.

The invention also relates to the promoter for plant asparagine synthetase which is induced by darkness and directs high levels of transcription.

2. BACKGROUND OF THE INVENTION

In higher plants, nitrogen assimilated from the soil must be incorporated into organic form for transport to the growing plant. The amides, asparagine and glutamine, are the two major nitrogen transport compounds in most higher plants (Sieciechowicz et al., 1988, Phytochemistry 27:663-671). These amides function to deliver nitrogen to and from plant organs at various stages of plant development. Since the production of asparagine and glutamine for nitrogen transport is crucial to plant growth, the enzymes involved in their synthesis are targets for herbicide action. Much is known about plant glutamine synthetase (GS) as an enzyme, a herbicide-target and as a gene family. In contrast, very little is known about plant asparagine synthetase (AS) at the biochemical level, at the herbicide-target level and nothing is known about the AS gene(s) in higher plants.

Asparagine is the major nitrogen transport compound which is synthesized when a plant is faced with excess ammonia rather than nitrate. During normal plant growth, conditions of ammonia excess arise when (1) plants are treated with externally applied fertilizers; (2) plants develop nitrogen-fixing root nodules; (3) the seed storage proteins of cotyledons are deaminated during germination; and (4) senescing plants are mobilizing nitrogen for seed formation. In certain species asparagine can account for up to 86% of transported nitrogen in the above contexts. See, Lea & Miflin, 1980, Transport And Metabolism Of Asparagine And Other Nitrogen Compounds Within The Plant, in The Biochemistry Of Plants, Volume 5, Ed. Miflin, Acad. Press, N.Y., Ch. 16.

There are several reasons why asparagine is preferred as a nitrogen transport/storage compound compared to glutamine in situations requiring the assimilation and transport of large amounts of nitrogen. Asparagine contains a high N:C ratio (2N:4C) compared to glutamine (2N:5C) which makes asparagine a more economical nitrogen transport/storage compound compared to glutamine. Asparagine is also a preferred compound for nitrogen transport/storage because it is relatively inert compared to glutamine. Because glutamine is such an active metabolite which donates the amide nitrogen to a large number of substrates, over-production of glutamine could seriously upset plant metabolism. Storage of high levels of nitrogen containing compounds is extremely important in vegetative structures such as fruits where asparagine stored in vacuoles serves as the primary source of nitrogen for seed storage protein synthesis in developing seeds.

Despite the crucial role of asparagine synthetase during plant development, very little is known about the AS enzyme in higher plants. Years of labor intensive biochemical investigations on plant AS have failed to produce a homogeneous enzyme preparation. The inability to purify AS biochemically is due, in part, to the fact that AS is extremely unstable in vitro in these partially purified extracts. In addition, AS activity is difficult to detect in partially purified extracts due to contaminating asparaginase activity, and due to the presence of specific non-protein inhibitors of AS activity.

2.1. MAMMALIAN, BACTERIAL AND YEAST ASPARAGINE SYNTHETASE

In contrast to the difficulties encountered in studies of plant AS enzyme, researchers have had more success studying AS in other systems. Methods for the purification of mammalian AS involve fractionation of the enzyme from the liver or pancreas of animals whose diets are altered to increase AS production in these organs. Methods involving ammonium sulfate frationation, ion exchange chromatography, affinity chromatography, and sucrose gradient centrifugation, have been reported for the partial purification of the mammalian AS enzyme. See, for example, Hongo, et al., 1978, Biochim. Biophys. Acta 522:258-266; Milman et al., 1979, Biochem. J. 181:51-59; Markin & Schuster, 1979, Biochem. Biophys. Res. Commun. 88(2):583-588; Hongo & Sato, 1981, Anal. Biochem. 114:163-166; and Hongo & Sato, 1983, Biochim. Biophys. Acta 742:484-489. Some researchers have used the partially purified mammalian AS preparation to generate monoclonal antibodies that define the enzyme in order to study mammalian AS (Pfeiffer et al., 1986, J. Biol. Chem. 261(4):1914-1919; Pfeiffer et al., 1987, J. Biol. Chem. 262 (24):11565-11570).

Somatic cell genetic studies assigned the structural gene for human AS to chromosome 7 (Arfin et al., 1983, Somatic Cell Genet. 9(5):517-531; Smith et al., 1984, Cytogen. Cell Genet. 37(1-4):585-586). Ultimately, cDNAs encoding mammalian AS were cloned (Ray et al., 1984, Gene 30:1-9; Andrulis et al., 1987, Mol. Cell Biol. 7:2435-2443); and very recently expressed in bacteria (Van Heeke & Schuster, 1989, J. Biol. Chem. 264 (10):5503-5509).

Bacteria have two forms of asparagine synthetase (AsnA and AsnB) (Humbert & Simoni, 1980, J. Bacteriol. 142:212-220; Nakamura, 1981, Nuc. Acids Res. 9(18):4669-4697; Scofield & Schuster, 198S, J. Cell Biol. 107:535a, Abstr. 3023). Bacterial AS has been cloned and transferred to mammalian cells in a complementation system, or as a dominant selectable marker (Waye et al., 1983, J. Mol. Appl. Genet. 2:69-82; Cartier et al., 1987, Mol. Cell. Biol. 71(5):1623-1628).

Yeast also have two genes for AS (ASN1 and ASN2) which have been defined genetically but have not been isolated or cloned (Jones, 1978, J. Bacteriol. 134:200-207; Ramos & Wiame, 1980, Eur. J. Biochem. 108:373-377).

2.2. PLANT ASPARAGINE SYNTHETASE

Attempts to purify plant AS using standard biochemical approaches have been largely unsuccessful. For example, attempted purification of AS from Lupin cotyledons and wheat seedlings using salt fractionation, negative absorption on alumina gel and gel filtration revealed that the enzyme is very labile and sensitive to high salt concentrations (Lea & Fowden, 1975, Proc. R. Soc. London B. 192:18-26; Rognes, 1975, Phytochem. 14:1975; Ramnefjell & Rognes, 1981, Suppl. Plant Physiol., Abstr. 244). Other schemes developed for purification of AS from soybean root nodules involving ammonium sulfate precipitation of crude extracts and chromatography of the supernatant on alumina gel and Reactive Blue 2-cross linked Agarose resulted in a preparation of low yield and limited stability (Huber & Streeter, 1985, Plant Science 42:9-17).

As a result of the inability to purify plant AS, studies of the enzyme in plants are largely confined to using assays designed to detect AS activity in various organs and/or subcellular locations within the plant during development. See, for example, Joy et al., 1983, Plant Physiol. 73:165-168; Shelp et al., 1984, Plant Science Letters 36:225-230; Huber & Streeter, 1984, Plant Physiol. 74:605-610; and Loyola-Vargas et al., 1988, J. Plant Physiol. 132: 289-293.

Unlike mammalian, bacterial and yeast systems, absolutely nothing is known about AS gene(s) in higher plants. Although auxotrophic mutants have been reported, the nature of these mutations has not been elucidated or genetically defined and, indeed, such analysis appears to be rather complex (Roth and Lark, 1984, Theor. Appl. Genet. 68:421-431).

3. SUMMARY OF THE INVENTION

The present invention relates to the cloning and expression of plant asparagine synthetase, an important enzyme involved in the formation of asparagine—a major nitrogen transport compound of higher plants. The invention also relates to the plant AS promoter which may be used to direct the expression of heterologous coding sequences. The AS promoter directs high levels of expression in nitrogen fixing root nodules, in cotyledons of germinating seeds, and dark-induced gene expression in leaves, stems and roots. This promoter can be used to direct the regulated expression of heterologous gene sequences in appropriate hosts.

To overcome the major problems encountered in the previous biochemical studies of plant AS, the present invention employs molecular techniques to directly isolate cDNA clones encoding plant AS. DNA sequence analysis of these cDNA clones revealed that plants contain at least two different AS mRNAs (AS1 and AS2) which encode homologous but distinct AS polypeptides. Full length cDNAs for plant AS can be used in a "reverse biochemical" approach to synthesize and characterize the encoded AS proteins. The ability to use the cloned plant AS cDNAs to synthesize the purified AS proteins will allow a characterization of the distinct plant AS enzyme(s) in terms of physical properties (i.e., substrate preference, ammonia or glutamine), herbicide sensitivity, and subcellular localization (i.e., plastid vs. cytosol).

The isolated cDNAs encoding plant AS may also be used to create herbicide resistant plants and salt/- drought tolerant plants, pathogen resistant plants or to develop novel herbicides or agents that synchronize plant cells in culture as described in more detail herein. For example, organisms which express the cloned plant AS cDNAs can be used to select for mutations in the AS gene(s) which produce an AS enzyme resistant to known AS inhibitors (for example, β aspartyl hydroxamate, albizziine, azaserine, etc.). Expression of such altered AS gene(s) or over-expression of wild-type AS gene(s) directed by a constitutive or inducible promoter in transgenic plants can produce plants resistant to known AS inhibitors. Additionally, over-expression of AS gene(s) in plants may confer salt/drought tolerance, or pathogen resistance.

Full length AS cDNA clones may also be used to synthesize highly purified preparations of the wild-type or altered AS enzyme in vitro or in vivo (e.g., in Asn⁻ bacteria, algae, neurospora, yeast, plant, or animal cells), or as a dominant selectable marker in any of these systems. In vitro or in vivo synthesized AS can be used as a substrate in a screen to identify novel herbicidal compounds, or cell cycle regulatory compounds which selectively inhibit this important but poorly understood plant enzyme.

3.1. DEFINITIONS

The following terms as used herein, whether in the singular or plural, shall have the meanings indicated.

| | |
|---|---|
| Asn = | asparagine |
| AS = | asparagine synthetase |
| bp = | base pair |
| EDTA = | disodium ethylene diamine tetracetate |
| GS = | glutamine synthetase |
| kb = | kilobase |
| SDS = | sodium dodecyl sulfate |
| 20 × SSC = | 175.3 g NaCl and 88.2 g sodium citrate in 800 ml $H_2O$, pH 7.0 (adjusted with 10 N NaOH), adjusted to 1 liter. |

4. DESCRIPTION OF THE FIGURES

FIG. 1. Restriction maps of cDNA clones and genomic clones, encoding AS1 and AS2. E=EcoRI, S=SstI, Bm=BamHI, Bg=BglII, H=HincII. E-- represents an EcoRi site in λcAS301 which was lost in the process of cloning and selection. Open bars represent the coding region of each cDNA:

FIG. 1a. pcAS1 (2.2 kb) is a composite full length cDNA constructed from restriction fragments (a, b and c) of overlapping cDNA clones (λcAS907, λcAS301 and λcAS305). λcAS301 and λcAS305 were isolated via heterologous hybridization to human AS cDNA (Andrulis et., al., 1987 Mol. Cell Biol. 7:2435-2443), while λcAS907 was synthesized as described in the examples.

Figure 1B:
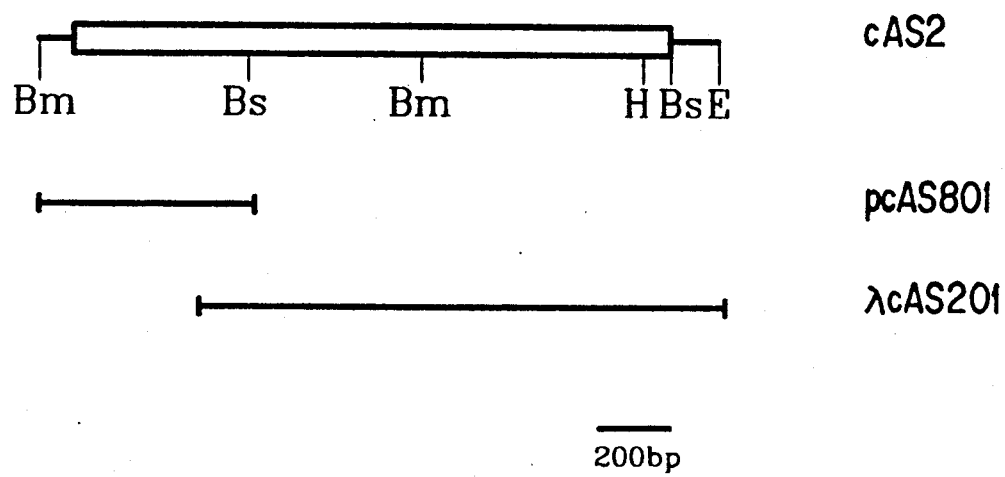

FIG. 1b. Overlapping cDNA clones pcAS801 and λcAS201 for AS2 mRNA were used to derive the restriction map of full-length cAS2. pcAS201 corresponds to a partial cDNA (1.5 kb) for AS2 mRNA (2.2kb) which was isolated by hybridization to AS2 genomic clone λgAS2 (FIG. 1C) which was obtained from a pea genomic library by cross-hybridization to AS1 cDNAs. λcAS801 was synthesized as described in the examples herein.

Figure 1C:
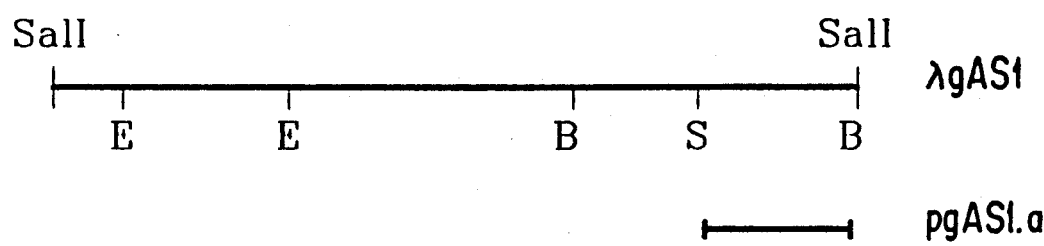
Figure 1D:
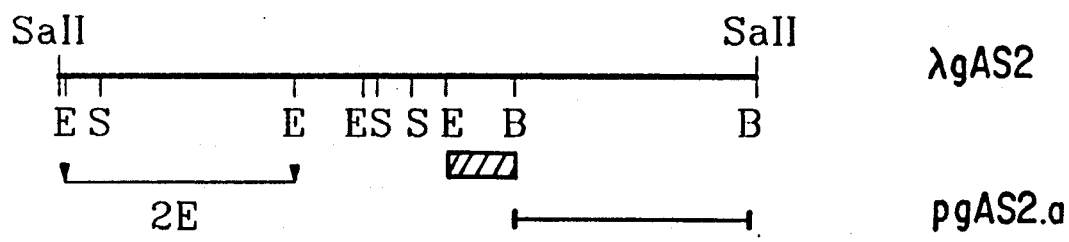

FIG. 1c and d. Restriction maps of lambda genomic clones λgAS1 and λgAS2 and their respective subcloned restriction fragments pgAS1.a and pgAS2.a. λgAS1 is a 17-18 kb SalI restriction fragment containing the pea AS1 gene. The line below λgAS1 denotes the 3.2 kb SstI-BamHI fragment subcloned into pTZ18U, called pgAS1.a. λgAS2 is a 16-17 kb SalI fragment containing the pea AS2 gene. The line below λgAS2 denotes a 5.5 kb BamHI fragment subcloned into pTZ18U, called pgAS2.a. The shaded bar under λgAS2 represents the 1.5 kb EcoRI-BamHI restriction fragment of λgAS2 which was used to isolate AS2 cDNAs. Arrows marked "2E" represent two EcoRI restriction sites which are not definitively mapped. E=EcoRI, B=BamHI, S=SstI. SalI sites marked correspond to sites derived from the λEMBL3 vector (Frischauf et al. 1983, J. Mol. Bio. 170, 827-842; Lycett et al 1985 Nuc. Acids Resh 3:6733-6743).

FIG. 2. Nucleotide sequences of cDNAs encoding pea AS1 and AS2.

FIG. 2a-2j. Nucleotide sequences of cDNAs pcAS1 (FIG. 2a-e) and cAS2 (FIG. 2f-j) are shown in the mRNA sense. The deduced amino acid sequence is denoted above the nucleotide sequence in the standard one letter code. Amino acids are numbered starting with the first inframe methionine as 1. 3' sequences extending beyond the pcAS1 cDNA insert (i.e., to residue number 2135 in FIG. 2e) derived from other overlapping cDNA clones are also shown. The translation termination codons in each clone are designated as "*".

FIG. 3 (parts a-d). Amino acid sequence homology of plant AS and human AS. The deduced amino acid sequences encoded by the Pisum sativum cDNA clones pcAS1 and cAS2, and human AS cDNA (pH131) (Andrulis et al., 1987, Mol. Cell Biol. 7:2435-2443) are compared. Amino acids are denoted in the standard one letter code. Double dots denote identities between pea AS1 and pea AS2 or the pea AS1 and human AS sequences as shown. Dashes in the amino acid sequences represent deletions used to maximize homology of AS proteins. Amino acid alignment is according to "fasta" computer program (Pearson and Lipman, 1988, Proc. Natl. Acad. Sci., USA, 85:2444-2448).

Figure 4A:
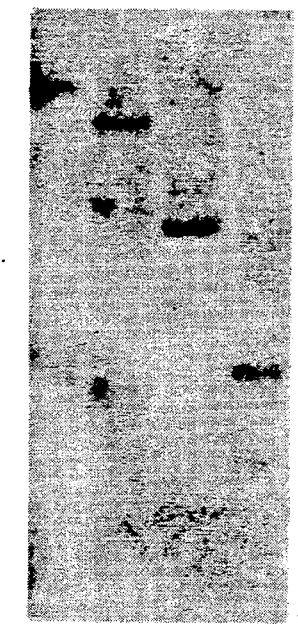
Figure 4B:
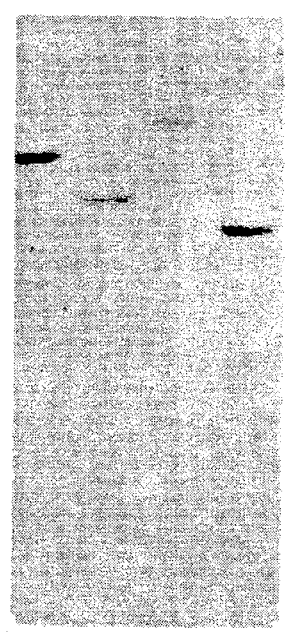

FIG. 4(parts a and b). Southern blot analysis of AS genes in Pisum sativum demonstrates that AS1 and AS2 are each encoded by a single nuclear gene in the pea genome. Pea nuclear DNA was digested with the following restriction enzymes: S=SstI (lanes 1 and 5), E=EcoRI (lanes 2 and 6), B=BamHI (lanes 3 and 7), and H=HindIII (lanes 4 and 8), resolved by gel electrophoresis, transferred to nitrocellulose, and probed with radioactive probes derived from the coding region of each cDNA pAS1 (FIG. 4A) or cAS2 (FIG. 4B) as described. In each digestion, a single radioactive band is detected by the DNA probe which corresponds to a single nuclear gene.

Figure 5A:
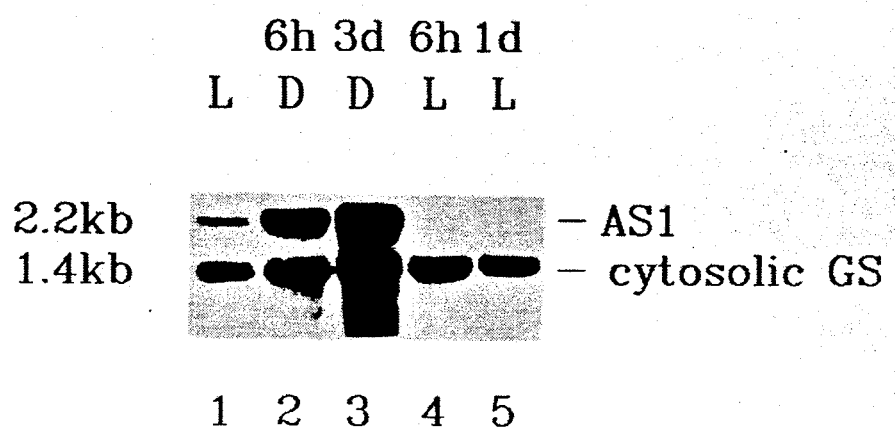

FIG. 5. Northern blot analysis demonstrates that AS1 mRNA accumulates to high levels in leaves in a "photophobic" fashion; i.e., AS1 mRNA accumulates in the dark. A gene-specific DNA probe from the 3, non-coding region of pcAS1 was used to probe AS1 mRNA (2.2 kb) in RNA from leaves of dark (D) or light (L) treated pea plants. As a control, mRNAs for chloroplast and cytosolic GS (1.5 and 1.4 kb, respectively) were also detected on the Northern blots with cDNA probes pGS185 and pGS299 (Tingey et al., 1988, J. Biol. Chem. 263(20):9651-9657):

FIG. 5a: Total RNA (20 μg) from leaves of peas grown in continuous white light for 14 days (lane 1), transferred to the dark for 6 hours (lane 2); or 3 days (lane 3) and back to continuous white light for 6 hours (lane 4) or 1 day (lane 5).

Figure 5B:
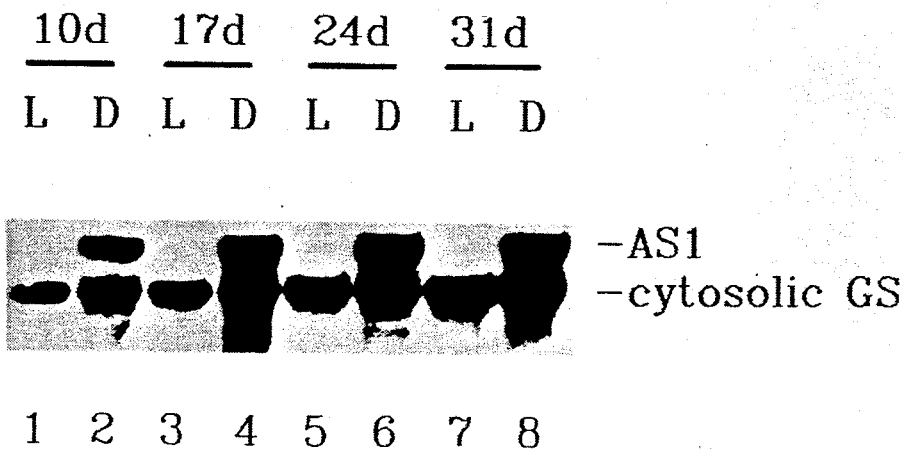

FIG. 5b: Total RNA (20 μg) from leaves of 10, 17, 24 and 31 day old plants. Controls were grown in continuous white light for 10, 17, 24 and 31 days ("L" lanes 1, 3, 5, and 7). Dark treated plants were grown in continuous white light for 7, 14, 21, 28 days and then transferred to the dark for an additional 3 days ("D" lanes 2, 4, 6, 8).

Figure 5C:
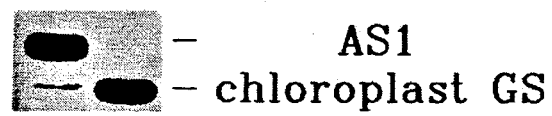

FIG. 5c: Total RNA (20 g) from leaves of pea plants grown in the dark for 7 days (lane 1) and transferred to the light for 72 hours (lane 2).

Figure 5D:

FIG. 5d. Total RNA (20 μg) from leaves of peas grown in normal light/dark cycle for 14 days (16 hours light, 8 hours dark) after which plants were collected during the day (light conditions) (lane 1), transferred to the dark for 4 days (lane 2) and back to continuous white-light for 24 hours (lane 3).

Figure 5E:

FIG. 5e: Total RNA (20 g) from leaves of peas grown in the dark for 9 days (lane 1) and subsequently treated with a pulse of red light then put back to the dark for 3 hours (lane 2), treated with a pulse of red light followed by a pulse of far-red light then put back into the dark for 3 hours (lane 3) or transferred to continuous white light for 8 hours (lane 4).

FIG. 6. Northern blot analysis of AS mRNA accumulation in cotyledons of germinating seedlings and in nitrogen fixing root nodules reveal that AS1 and AS2 mRNAs accumulate in contexts of increased nitrogen transport. Gene specific DNA fragments from the 3' non-coding region of pcAS1 or cAS2 were used to detect AS1 mRNA (2.2 kb) AS2 mRNA (2.2 kb) on Northern blots. As a control, mRNA for the β-subunit of mitochondrial ATPase (2.1 kb) was monitored (Boutry & Chua, 1985, EMBO J. 4(9):2159–2166):

FIG. 6a: Total RNA (20 μg) extracted from cotyledons of pea seedlings germinated 2 to 18 days (lanes 1–8).

FIG. 6b: RNA extracted from roots as follows: 1 μg polyadenylated RNA isolated from roots of uninfected pea plants (lane 1) or nitrogen fixing root nodules (lane 2).

Figure 7:
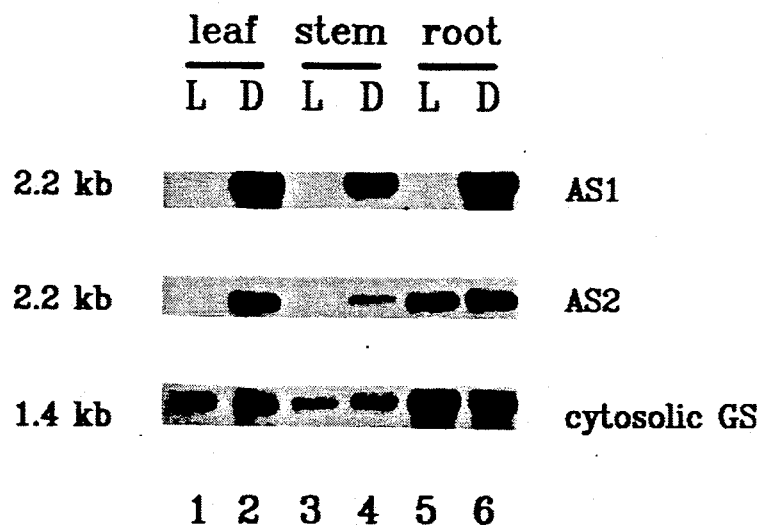

FIG. 7: Dark-Induced expression of AS mRNA occurs independent of organ-type Northern blot analysis was performed to detect the effect of the light on steady-state levels of AS mRNA in leaves, stems and roots. Pea plants were grown in continuous light for 28 days (L, Lanes 1, 3, 5) or grown in continuous light for 25 days and transferred to the dark for 3 days (D, lanes 2, 4, 6). Total RNA was isolated from leaves (lanes 1 and 2), stems (lanes 3 and 4), and roots (lanes 5 and 6) of either light-grown (L) or dark-adapted (D) plants. Gene-specific probes from the 3' non-coding region of AS1 and AS2 cDNAs were used to detect AS mRNA (2.2 kb). As a control, cytosolic GS (1.4 kb) mRNA was also monitored on the Northern blot (Tingey et al., 1987, EMBO J. 6:1–9). These results demonstrate that the dark-induced accumulation of AS1 and AS2 mRNA occurs independent of organ-type.

FIG. 8(parts a–c). Circadian rhythm is not involved in the dark-induced expression of AS1 gene. Pea plants were grown under a normal light/dark cycle (16 hours of light and 8 hours of dark) for 18 days. On the 19th day, some of the plants were kept in the normal light/dark cycle (A), some of the plants were kept in extended darkness for a total of 18 hours (B), and others were kept in extended light condition instead of darkness (C). Leaves were collected every 3 hours on the 19th day and used for isolating total RNA. Gene-specific Northern blot analyses were performed to detect the steady-state levels of AS1 mRNA. As a control, mRNA levels of cytosolic GS were detected in the same blots. Empty boxes represent light period, and black boxes represent dark period.

Figure 9:
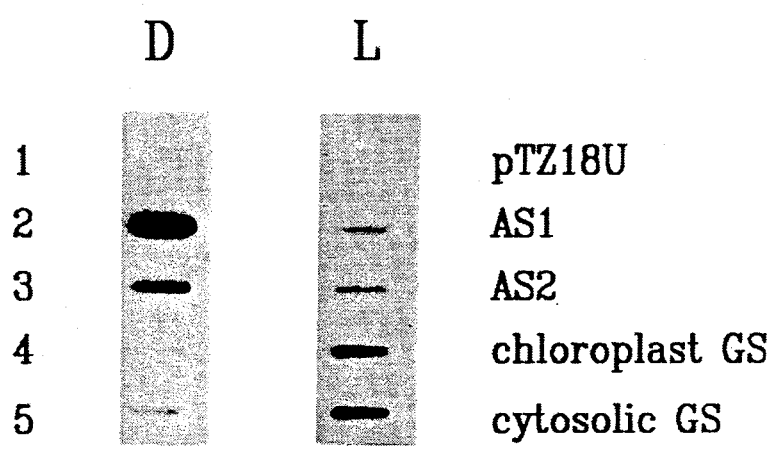

FIG. 9. Dark-induced expression of AS genes is regulated at the transcriptional level. Transcriptional analysis of AS genes in pea leaves was assayed in nuclear run-on experiments. Nuclei isolated from leaves of dark-adapted (D) or light-grown (L) pea plants were used to perform nuclear run-on assays with $^{32}$P-ATP (Hagen et al., 1985, Mol. Cell. Biol. 5:1197–1203; Kuo et al., 1988, Mol. Cell. Biol. 8:4966–4971). Slot-blot filters containing the AS1 and AS2 cDNA clones, positive controls (cDNA clones of chloroplast GS and cytosolic GS), and a negative control (pTZ18U) were used to detect specific $^{32}$P-labeled transcripts generated in the nuclear run-on reactions. These results demonstrate that the dark-induced expression of AS genes is regulated at the transcriptional level.

FIG. 10 (parts a–c). Nucleotide sequence of the AS1 promoter numbered according to the transcription start site. The 5' upstream sequence of AS1 gene is shown and nucleotide number 1 corresponds to the transcription start site. The "TATA" element at nucleotide number −30 is boxed.

Figure 11:
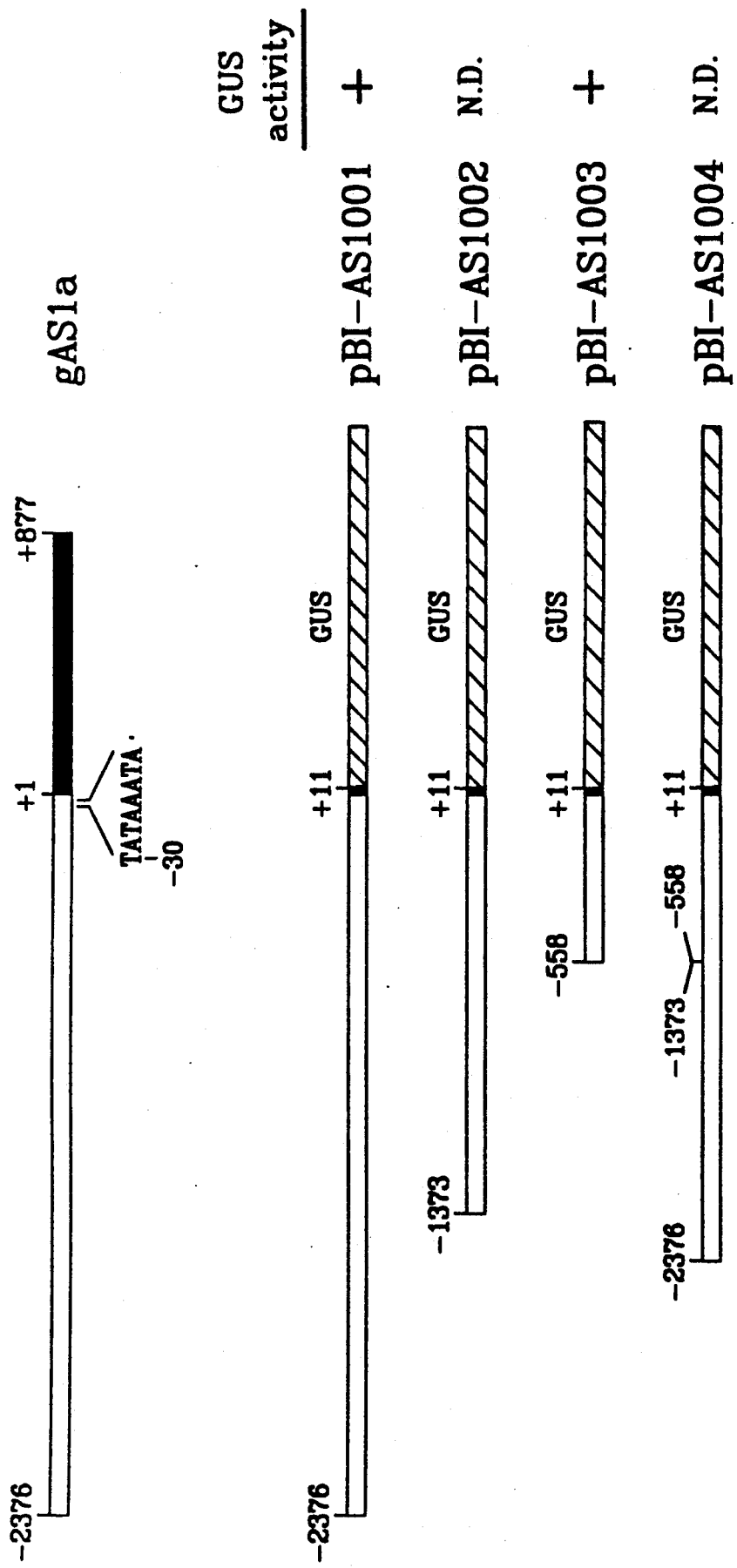

FIG. 11. Deletion analysis of the AS1 promoter defines regions of DNA required for expression in vivo. Different regions of the 5' upstream sequence of the AS1 gene were subcloned into pBI101.1 plasmid in a transcriptional fusion with the GUS reporter gene (Jefferson et al., 1987, EMBO J. 6:3901–3907). AS-GUS constructs were introduced into transgenic plants via Agrobacterium mediated DNA transfer (Horsch et al., 1985, Science 227:1229–1231). gAS1a is a genomic fragment containing DNA sequences of the AS1 gene from nucleotide −2376 to +877 (+1 represents the transcription initiation site). Regions of the AS1 promoter were fused to GUS as follows: construct pBI-AS1001 contains nucleotides −2376 to +11 of the AS1 promoter; construct pBI-AS1002 contains nucleotides −1373 to +11 of the AS1 promoter; and construct pBI-AS1003 contains nucleotides −558 to +11 of the AS1 promoter. For construct pBI-1004, an internal fragment from nucleotide −1373 to −558 of the AS1 promoter was deleted. The ability of each AS promoter fragment to direct expression of the GUS reporter gene was monitored by GUS activity assay performed on leaves of dark-adapted transgenic tobacco (Jefferson et al., 1987, Plant. Mol. Biol. Reporter 5:387–405). "+" represents the constructs in which GUS activity was detected in transgenic plants. The GUS activity for pBI-AS1002 and pBI-AS1004 have not yet been determined (N.D.).

FIG. 12(parts a and b). Nucleotide sequence of the AS2 promoter. The 5' upstream sequence of the AS2 gene was determined by sequencing serial deletion clones of the gAS2a BamHI-BamHI genomic insert. Nucleotide number 1 represents the end of one deletion clone used for sequencing. The putative "TATA" element at nucleotide 989 is boxed, and the 5' end of AS2 cDNA is marked by an arrow.

FIG. 13. The AS1 and AS2 promoters contain conserved sequence elements which may be involved in the regulation of transcription. Conserved DNA sequences between AS1 and AS2 promoters are shown. The 569 nucleotides of the AS1 promoter (−558 to +11) were compared to the entire AS2 promoter sequence shown in FIG. 12. Conserved sequences shown in FIG. 13 were detected using computer program DNASIS.

5. DESCRIPTION OF THE INVENTION

The present invention relates to the cloning and expression of biologically active plant AS, an important but poorly understood enzyme involved in the formation of asparagine—one of the major nitrogen transport compounds of higher plants. The invention also relates to the plant AS promoter which directs high levels of expression in nitrogen fixing root nodules, in cotyledons of germinating seeds, and dark-induced gene expression in leaves, stems and roots. This promoter can be used to direct the regulated expression of heterologous gene sequences in appropriate hosts.

In accordance with one aspect of the invention, biologically active plant AS may be produced by the cloning and expression of the nucleotide coding sequence for plant AS or its functional equivalent in appropriate host cells. Successful expression and production of purified plant AS using the full length cDNA clones described and exemplified herein is particularly significant since this enzyme has yet to be purified to homogeneity from plants despite years of intensive biochemical investigation due to a number of factors present in the plant extracts. E.g., the extreme instability of AS in partially purified plant extracts; the presence of contaminating asparaginase activity in the plant extracts making it difficult to assay for AS activity; and the presence of specific AS inhibitors in the plant extracts.

The synthesis of purified plant AS enzyme via genetic engineering techniques which provide for the expression of full length cDNAs may be utilized to obtain antibodies specific for plant AS which will enable the further characterization of the distinct forms and subcellular localizations of AS enzymes in plant cells. In particular, the subcellular localization of plant AS to the plastids would be significant since a plastid isoform of plant AS may have very different properties in terms of herbicide resistance as compared to cytosolic isoforms of AS. Such studies, if attempted with antibodies that define mammalian AS could not be used to address these issues. The ability to distinguish plastid and cytosolic isoforms of AS, and to identify herbicides that specifically inhibit the plastid isoform, but not cytosolic AS or human AS, is important for designing herbicides that are not toxic or harmful to humans and animals. In general, herbicides in current use are inhibitors of enzymes involved in the formation of essential amino acids, i.e., enzymes and amino acids which are not produced by animals. The ability to develop herbicides that inhibit only chloroplast isoforms of enzymes such as AS or GS (i.e., enzymes involved in the formation of nonessential amino acids) but do not inhibit cytosolic AS or human AS, would vastly expand the repertoire of herbicides which could be used having greater efficacy and less toxicity to humans.

The plant AS cDNA clones described herein also can be used to engineer herbicide resistant plants, salt/-drought tolerant plants, and pathogen resistant plants, or to screen and select novel herbicides or agents which synchronize cells in culture. For example, AS cDNAs genetically altered in vitro or in vivo can be used to produce altered AS enzymes which are resistant to known AS inhibitors. Such genes can be engineered into transgenic plants to confer herbicide resistance to the plant. Similarly, herbicide resistance, salt tolerance or drought tolerance may be conferred by engineering the over-expression of wild-type or altered AS in transgenic plants so that asparagine is overproduced. Expression of such wild type or altered AS can be used as a dominant selectable marker in a variety of organisms. Alternatively, the cloned plant AS cDNAs expressed by microorganisms can be used to screen and identify new herbicidal compounds, or cell cycle inhibitors that selectively inhibit the AS holoenzyme.

The invention may be divided into the following stages solely for the purpose of description: (a) isolation or generation of the coding sequence for plant AS gene(s); (b) construction of an expression vector which will direct the expression of the plant AS coding sequences; (c) transfection of appropriate hosts which are capable of replicating and expressing the plant AS coding sequences to produce biologically active gene products; and (d) identification and/or purification of the plant AS so produced. Once a transformant or transfectant is identified that expresses high levels of biologically active plant AS, the practice of the invention involves the expansion of that clone and the use of that clone in the production of plant AS enzymes, the selection of novel herbicides, and/or the engineering of transgenic plants.

Another aspect of the invention involves the use of the plant AS promoter to direct the expression of heterologous coding sequences. The AS promoter directs high levels of expression in nitrogen fixing root nodules, in cotyledons of germinating seeds, and dark-induced gene expression in leaves, stems and roots. This promoter can be used to direct the regulated expression of heterologous gene sequences in appropriate hosts.

The invention is demonstrated herein, by way of examples in which cDNAs of plant AS were prepared, cloned and characterized. Sequence analysis of the plant AS cDNA clones, which were isolated using heterologous DNA probes encoding human AS, revealed two different plant AS cDNAs that encode homologous but distinct plant AS polypeptides, AS1 and AS2. The organ-specific and "photophobic" expression of AS1 and AS2 mRNAs in higher plants in vivo is also described. Genomic clones of AS containing the plant AS photophobic promoter were also prepared, cloned and sequenced.

Various aspects of the invention are described in more detail in the subsections below and in the examples that follow.

5.1. PLANT ASPARAGINE SYNTHETASE CODING SEQUENCE

The nucleotide coding sequences and deduced amino acid sequences for plant AS1 and AS2 are depicted in FIG. 2 (FIG. 2A and 2B, respectively). These nucleotide sequences, or fragments or functional equivalents thereof, may be used to generate recombinant DNA molecules that direct the expression of the AS1 or AS2 gene product, or functionally active peptides or functional equivalents thereof, in appropriate host cells.

Due to the degeneracy of the nucleotide coding sequences, other DNA sequences which encode substantially the same amino acid sequences as depicted in FIGS. 2A and 2B may be used in the practice of the present invention for the cloning and expression of plant AS. Such alterations include deletions, additions or substitutions of different nucleotide residues resulting in a sequence that encodes the same or a functionally equivalent gene product. The gene product may contain deletions, additions or substitutions of amino acid residues within the sequence, which result in a silent change thus producing a bioactive product. Such amino acid substitutions may be made on the basis of similarity in polarity, charge, solubility, hydrophobicity, hydrophilicity and/or the amphipathic nature of the residues involved. For example, negatively charged amino acids include aspartic acid and glutamic acid; positively charged amino acids include lysine and arginine; amino acids with uncharged polar head groups having similar hydrophilicity values include the following: leucine, isoleucine, valine; glycine, alanine; asparagine, glutamine; serine, threonine; phenylalanine, tyrosine.

The genomic sequences for plant AS may be obtained from any plant cell source, whereas mRNA for preparation of cDNA copies may be obtained from cell sources that produce AS. For example, parts of plants (e.g., leaves, stems, roots, nodules, cotyledons, seeds, fruits, etc.) may be ground and used as the source for extracting DNA or RNA. Alternatively, plant cell lines can be used as a convenient source of DNA or RNA. Genetically engineered microorganisms or cell lines containing plant AS coding sequences, such as the deposited embodiments described herein, may be used as a convenient source of DNA for this purpose.

The AS coding sequence may be obtained by cDNA cloning of RNA isolated and purified from such cellular sources or by genomic cloning. Either cDNA or genomic libraries may be prepared from the DNA fragments generated using techniques well known in the art, including but not limited to the use of restriction enzymes. The fragments which encode plant AS may be identified by screening such libraries with a nucleotide probe that is substantially complementary to any portion of the sequences depicted in FIG. 2. Although portions of the coding sequence may be utilized, full length clones, i.e, those containing the entire coding region for AS, may be preferable for expression. To these ends, techniques well known to those skilled in the art for the isolation of DNA, generation of appropriate restriction fragments, construction of clones and libraries, and screening recombinants may be used. For a review of such techniques see, for example, Maniatis et al., 1982, Molecular Cloning A Laboratory Manual, Cold Spring Harbor Press, N.Y., Chapters 1-11. Alternatively, oligonucleotides derived from AS1 or AS2 sequences could be used as heterologous primers in PCR (polymerase chain reactions) to generate cDNA or genomic copies of AS sequences from other species. For a review of such PCR techniques, see for example, Gelfand, D. H., 1989, "PCR Technology. Principles and Applications for DNA Amplification," Ed., H. A. Erlich, Stockton Press, N.Y.; and "Current-Protocols in Molecular Biology," Vol. 2, Ch. 15, Eds. Ausubel et al., John Wiley & Sons, 1988.

In an alternate embodiment of the invention, the coding sequence of FIG. 2A or 2B could be synthesized in whole or in part, using chemical methods well known in the art. See, for example, Caruthers, et al., 1980, Nuc. Acids Res. Symp. Ser. 7:215-233; Crea and Horn, 180, Nuc. Acids Res. 9(10): 2331; Matteucci and Caruthers, 1980, Tetrahedron Letters 21:719; and Chow and Kempe, 1981, Nuc. Acids Res. 9(12) 2807-2817. Alternatively, the protein itself could be produced using chemical methods to synthesize the amino acid sequence depicted in FIG. 2A or FIG. 2B in whole or in part. For example, peptides can be synthesized by solid phase techniques, cleaved from the resin, and purified by preparative high performance liquid chromatography. (E.g., see, Creighton, 1983, Proteins Structures And Molecular Principles, W. H. Freeman and Co., N.Y. pp. 50-60). The composition of the synthetic peptides may be confirmed by amino acid analysis or sequencing (e.g., the Edman degradation procedure; see Creighton, 1983, Proteins, Structures and Molecular Principles, W. H. Freeman and Co., N.Y., pp. 34-49).

In the specific embodiments described in the examples herein, the plant AS coding sequence was obtained by direct cloning of AS cDNAs from *Pisum sativum* using a heterologous DNA probe for human AS. Nucleotide sequence analysis of these cDNAs demonstrate that peas contain two homologous but distinct AS mRNAs, AS1 and AS2 (FIGS. 1 and 2). The two distinct cDNAs (pcAS1 and pcAS2) encode homologous but distinct AS polypeptides. Homology between plant AS and human AS was determined to be approximately 47%, demonstrating that human and plant AS are evolutionarily related, yet quite distinct molecules (FIG. 3, and Section 6.2.2 at Table II, infra). Southern blot analysis of pea nuclear DNA revealed that AS is encoded by a small gene family in peas consisting of at least two genes, AS1 and AS2 (FIG. 4). Northern blot analysis of pea RNA revealed that the AS1 and AS2 mRNAs accumulate differentially during plant development (FIGS. 5 and 6).

There are numerous developmental contexts where high levels of asparagine are synthesized for nitrogen transport. When plants are grown in the dark, asparagine is the preferred nitrogen transport compound compared to glutamine since it has a high N:C ratio, making it a more economical compound for nitrogen transport and storage under growth conditions where carbon skeletons are limited. Consistent with these physiological findings, our analysis of AS mRNA has shown that AS1 mRNA accumulates to high levels in leaves of dark-grown or dark-adapted plants (FIG. 5) and in roots and stems (FIG. 7). AS1 mRNA accumulates to high levels within as little as 3 hours of darkness. Thus the "photophobic" accumulation of AS1 mRNA is physiologically significant for plants grown in a short dark cycle (i.e., at night). In contrast, AS2 mRNA is present at low levels in leaves of light or dark grown plants.

Asparagine is also the preferred nitrogen transport/storage compound in two other developmental contexts where large amounts of nitrogen must be mobilized, namely in the transport of nitrogen out of cotyledons to the seedling during germination, and the transport of newly fixed nitrogen out of root nodules to the rest of the plant. In the majority of seeds, nitrogen is stored in the cotyledons as insoluble proteins called seed storage proteins. During germination, these seed storage proteins provide a ready reserve of nitrogen for the growing seedling. The amino acids produced by hydrolysis of the storage proteins in the cotyledons are rarely transported out of the cotyledons as such. The released amino acids are first deaminated, and the majority of the ammonia is transported out of the cotyledons as either glutamine or asparagine. A classic example of asparagine synthesis occurs in lupin where 86.5% of the nitrogen from seed storage protein is converted into asparagine. Asparagine is also the major amino acid transported out of cotyledons in germinating cotton seedlings, wheat grains (Garg et al 1984, J. Agricult. Food Chem. 32 (3):519-523 , soybean, maize (Oaks & Ross, 1984, Can J. Bot. 62 (10): 68-73), and apple seeds. For review, see Lea & Miflin, 1980, Transport And Metabolism Of Asparagine And Other Nitrogen Compounds Within the Plant, in The Biochemistry Of Plants, Vol. 5, Ed. Miflin, Acad. Press, N.Y., Ch. 16.

We have shown that the pivotal role of asparagine in cotyledons of germinating peas is reflected at the molecular level. mRNAs for both AS1 and AS2 accumulate to high levels in cotyledons of germinating pea seedlings (FIG. 6A). In amide-transporting legumes (e.g., peas, alfalfa) the majority of newly fixed ammonia is transported out of nitrogen-fixing root nodules as glutamine or asparagine. AS shows the most dramatic increase in activity when the enzymes of N-metabolism are examined in alfalfa root nodules. The role of AS in asparagine synthesis in nodules is also reflected at the molecular level. As demonstrated herein, AS1 and AS2 mRNAs accumulate to high levels in nitrogen fixing root nodules of pea, where newly fixed ammonia must be transported from the root nodules to the developing plant (FIG. 6B).

5.2. EXPRESSION OF PLANT ASPARAGINE SYNTHETASE

In order to express a biologically active plant AS, the nucleotide sequence coding for plant AS, or a functional equivalent as described in Section 5.1 supra, is inserted into an appropriate expression vector, i.e., a vector which contains the necessary elements for the transcription and translation of the inserted coding sequence. The plant AS gene product as well as host cells, cell lines or plants transfected or transformed with recombinant AS expression vectors can be used for a variety of purposes. These include but are not limited to generating antibodies (i.e. monoclonal or polyclonal) that define plant AS; creating mutant AS enzymes which are resistant to herbicides; creating transgenic plants containing such herbicide resistant mutant AS genes; or creating transgenic plants which over-express AS and demonstrate herbicide resistance, salt/drought tolerance and/or pathogen resistance; screening and selecting for novel AS inhibitors which may be used as herbicides, and/or cell cycle regulators for synchronizing plant cells in culture.

5.2.1. CONSTRUCTION OF EXPRESSION VECTORS CONTAINING THE PLANT AS CODING SEQUENCE

Methods which are well known to those skilled in the art can be used to construct expression vectors containing the AS coding sequence and appropriate transcriptional/translational control signals. These methods include in vitro recombinant DNA techniques, synthetic techniques and in vivo recombination/genetic recombination. See, for example, the techniques described in Maniatis et al., 1982 Molecular Cloning A Laboratory Manual, Cold Spring Harbor Laboratory, N.Y., Chapter 12.

A variety of host-expression vector systems may be utilized to express the plant AS coding sequence. These include but are not limited to microorganisms such as bacteria transformed with recombinant bacteriophage DNA, plasmid DNA or cosmid DNA expression vectors containing the plant AS coding sequence; yeast transformed with recombinant yeast expression vectors containing the plant AS coding sequence; insect cell systems infected with recombinant virus expression vectors (e.g., baculovirus) containing the plant AS coding sequence; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing the plant AS coding sequence; or animal cell systems infected with recombinant virus expression vectors (e.g., adenovirus, vaccinia virus) containing the plant AS coding sequence.

The expression elements of these vectors vary in their strength and specificities. Depending on the host/vector system utilized, any of a number of suitable transcription and translation elements, including constitutive and inducible promoters, may be used in the expression vector. For example, when cloning in bacterial systems, inducible promoters such as pL of bacteriophage $\lambda$, plac, ptrp, ptac (ptrp-lac hybrid promoter) and the like may be used; when cloning in insect cell systems, promoters such as the baculovirus polyhedrin promoter may be used; when cloning in plant cell systems, promoters derived from the genome of plant cells (e.g., heat shock promoters; the promoter for the small subunit of RUBISCO; the promoter for the chlorophyll a/b binding protein) or from plant viruses (e.g., the 35S RNA promoter of CaMV; the coat protein promoter of TMV) may be used; when cloning in mammalian cell systems, promoters derived from the genome of mammalian cells (e.g., metallothionein promoter) or from mammalian viruses (e.g., the adenovirus late promoter; the vaccinia virus 7.5K promoter) may be used. Promoters produced by recombinant DNA or synthetic techniques may also be used to provide for transcription of the inserted plant AS coding sequence.

In bacterial systems a number of expression vectors may be advantageously selected depending upon the use intended for the plant AS expressed. For example, when large quantities of AS are to be produced for the generation of AS antibodies, vectors which direct the expression of high levels of fusion protein products that are readily purified may be desirable. Such vectors include but are not limited to the *E. coli* expression vector pUR278 (Ruther et al., 1983, EMBO J. 2:1791), in which the plant AS coding sequence may be ligated into the vector in frame with the lac Z coding region so that a hybrid AS-lac Z protein is produced; pIN vectors (Inouye & Inouye, 1985, Nucleic acids Res. 13:3101-3109; Van Heeke & Schuster, 1989, J. Biol. Chem. 264:5503-5509); and the like. However, where the plant AS expression vector is to be used in an Asn⁻ host for complementation assays described infra, the expression of unfused AS using expression vectors with few or no host genotype requirements, including, but not limited to vectors such as ptac12, (Amann et al., 1983, Gene 25:167) and the like may be preferred.

In yeast, a number of vectors containing constitutive or inducible promoters may be used. For a review see, Current Protocols in Molecular Biology, Vol. 2, 1988, Ed. Ausubel et al., Greene Publish. Assoc. & Wiley Interscience, Ch. 13; Grant et al., 1987, Expression and Secretion Vectors for Yeast, in Methods in Enzymology, Eds. Wu & Grossman, 31987, Acad. Press, N.Y., Vol. 153, pp.516-544; Glover, 1986, DNA Cloning, Vol. II, IRL Press, Washington, D.C., Ch. 3; and Bitter, 1987, Heterologous Gene Expression in Yeast, Methods in Enzymology, Eds. Berger & Kimmel, Acad. Press, N.Y., Vol. 152, pp. 673-684; and The Molecular Biology of the Yeast Saccharomyces, 1982, Eds. Strathern et al., Cold Spring Harbor Press, Vols. I and II. For complementation assays in yeast, pea cDNAs for AS may be cloned into yeast episomal plasmids (YEp)

which replicate autonomously in yeast due to the presence of the yeast 2μ circle. The plant AS sequence may be cloned behind either a constitutive yeast promoter such as ADH or LEU2 or an inducible promoter such as GAL (Cloning in Yeast, Chpt. 3, R. Rothstein In: DNA Cloning Vol.11, A Practical Approach, Ed. DM Glover, 1986, IRL Press, Eash., D.C.). Constructs may contain the 5' and 3' non-translated regions of the cognate plant mRNA or those corresponding to a yeast gene. YEp plasmids transform at high efficiency and the plasmids are extremely stable. Alternatively vectors may be used which promote integration of foreign DNA sequences into the yeast chromosome.

In cases where plant expression vectors are used, the expression of the plant AS coding sequence may be driven by any of a number of promoters. For example, viral promoters such as the 35S RNA and 19S RNA promoters of CaMV (Brisson et al., 1984, Nature 310:511-514), or the coat protein promoter of TMV (Takamatsu et al., 1987, EMBO J. 6:307-311) may be used; alternatively, plant promoters such as the small subunit of RUBISCO (Coruzzi et al., 1984, EMBO J. 3:1671-1680; Broglie et al., 1984, Science 224:838-843); or heat shock promoters, e.g., soybean hsp17.5-E or hsp17.3-B (Gurley et al., 1986, Mol. Cell. Biol. 6:559-565) may be used. These constructs can be introduced into plant cells using Ti plasmids, Ri plasmids, plant virus vectors, direct DNA transformation, microinjection, electroporation, etc. For reviews of such techniques see, for example, Weissbach & Weissbach, 1988, Methods for Plant Molecular Biology, Academic Press, NY, Section VIII, pp. 421-463; and Grierson & Corey, 1988, Plant Molecular Biology, 2d Ed., Blackie, London, Ch. 7-9.

An alternative expression system which could be used to express plant AS is an insect system. In one such system, *Autographa californica* nuclear polyhedrosis virus (AcNPV) is used as a vector to express foreign genes. The virus grows in *Spodoptera frugiperda* cells. The plant AS coding sequence may be cloned into non-essential regions (for example the polyhedrin gene) of the virus and placed under control of an AcNPV promoter (for example the polyhedrin promoter). Successful insertion of the plant AS coding sequence will result in inactivation of the polyhedrin gene and production of non-occluded recombinant virus (i.e., virus lacking the proteinaceous coat coded for by the polyhedrin gene). These recombinant viruses are then used to infect *Spodoptera frugiperda* cells in which the inserted gene is expressed. (E.g., see Smith et al., 1983, J. Viol. 46:584; Smith, U.S. Pat. No. 4,215,051).

In cases where an adenovirus is used as an expression vector, the plant AS coding sequence may be ligated to an adenovirus transcription/translation control complex, e.g., the late promoter and tripartite leader sequence. This chimeric gene may then be inserted in the adenovirus genome by in vitro or in vivo recombination. Insertion in a nonessential region of the viral genome (e.g., region E1 or E3) will result in a recombinant virus that is viable and capable of expressing plant AS in infected hosts. (E.g., See Logan & Shenk, 1984, Proc. Natl. Acad. Sci. (USA) 81:3655-3659). Alternatively, the vaccinia 7.5K promoter may be used. (E.g., see Mackett et al., 1982, Proc. Natl. Acad. Sci. (USA) 79:7415-7419; Mackett et al., 1984, J. Virol. 49:857-864; Panicali et al., 1982, Proc. Natl. Acad. Sci. 79:4927-4931).

Specific initiation signals may also be required for efficient translation of inserted AS coding sequences. These signals include the ATG initiation codon and adjacent sequences. In cases where the entire AS gene, including its own initiation codon and adjacent sequences, are inserted into the appropriate expression vectors, no additional translational control signals may be needed. However, in cases where only a portion of the AS coding sequence is inserted, exogenous translational control signals, including the ATG initiation codon, must be provided. Furthermore, the initiation codon must be in phase with the reading frame of the AS coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see Bitter et al., 1987, Methods in Enzymol. 153:516-544).

In addition, a host cell strain may be chosen which modulates the expression of the inserted sequences, or modifies and processes the gene product in the specific fashion desired. Expression driven by certain promoters can be elevated in the presence of certain inducers, (e.g., zinc and cadmium ions for metallothionein promoters). Therefore, expression of the genetically engineered plant AS may be controlled. This is important if the protein product of the cloned foreign gene is lethal to host cells. Furthermore, modifications (e.g., glycosylation) and processing (e.g., cleavage) of protein products may be important for the function of the protein. Different host cells have characteristic and specific mechanisms for the post-translational processing and modification of proteins. Appropriate cells lines or host systems can be chosen to ensure the correct modification and processing of the foreign protein expressed.

One way to select for the expression of a biologically active plant AS gene product, be it wild type, mutated or altered, and/or to screen for new herbicides, is to introduce an appropriate expression vector containing the AS coding sequence into asparagine minus (Asn⁻) host cell strains (of bacteria, algae, neurospora, yeast, higher plants or animals) which are grown in selective asparagine minus media, as in the complementation assay described infra. The ability of an AS cDNA to confer asparagine independent growth to the host cells, i.e., complement the host cells, indicates the expression and formation of an active holoenzyme. A number of different (Asn⁻) host cell strains may be used for this purpose including but not limited to asnA⁻, asnB⁻ strains of *E. coli*, JE6279 (Nakamura, et al., 1981, Nuc. Acids Res. 9:4669-4676) or ER (Kaguni et al., 1979 Proc. Natl. Acad. Sci. (USA) 76:6250-6254): neurospora Asn hosts (MacPhee et al., 1983, J. Bacteriol. 156:457-478); asn1⁻, asn2⁻ yeast host cells such as XE299-1A XE293-8B, or XE293-8D (Jones et al., 1978, J. Bacteriol. 134:200-207); and plant cell lines such as the gln⁻ asn⁻ soybean cell line (Roth & Lark, 1982, Plant Cell Reports 1:157-160), to name but a few. Heterologous host systems may require the use of a second selectable marker as a means for selecting incorporation of the vector, e.g., in cases where plant AS may not complement the Asn⁻ auxotroph. To this end, rescue of auxotrophy for another amino acid in addition to Asn (e.g., histidine) can be used as the selectable marker; alternatively, dominant selectable markers such as dhfr and resistance to methotrexate, thymidine kinase activity, etc. described infra. may be used. For example, the yeast YEp plasmids have been constructed to contain a number of different selectable marker genes such as: his3, ura3, leu2 or trpl (Ma et al., 1987, Gene 58: 201–216). Yeast strains harboring the auxotrophy compatible with one of these YEp vectors may be crossed into an asn⁻ strain, e.g., XE293-8B or 8D (Jones, 1978, J. Bacteriol. 134:200–207) using standard yeast genetic techniques. The yeast strain harboring the asn⁻ phenotype and marker auxotrophy is transformed with the YEp vector containing plant AS; asn⁺ colonies may then be selected and characterized.

5.2.2. IDENTIFICATION OF TRANSFECTANTS OR TRANSFORMANTS EXPRESSING THE PLANT AS GENE PRODUCT AND ISOLATION OF PLANT AS

The host cells which contain the plant AS coding sequence and which express the biologically active AS gene product may be identified by at least four general approaches: (a) DNA-DNA hybridization; (b) the presence or absence of "marker" gene functions; (c) assessing the level of transcription as measured by the expression of AS mRNA transcripts in the host cell; and (d) detection of the AS gene product as measured by immunoassay or by its biological activity; (e) phenotypic rescue; or (f) resistance to herbicides.

In the first approach, the presence of the plant AS coding sequence inserted in the expression vector can be detected by DNA-DNA hybridization using probes comprising nucleotide sequences that are homologous to the plant AS coding sequence substantially as shown in FIG. 2A or 2B or portions or derivatives thereof.

In the second approach, the recombinant expression vector/host system can be identified and selected based upon the presence or absence of certain "marker" gene functions (e.g., thymidine kinase activity, resistance to antibiotics, resistance to methotrexate, transformation phenotype, occlusion body formation in baculovirus, etc.). For example, if the plant AS coding sequence in inserted within a marker gene sequence of the vector, recombinants containing the plant AS coding sequence can be identified by the absence of the marker gene function. Alternatively, a marker gene can be placed in tandem with the plant AS sequence under the control of the same or different promoter used to control the expression of the plant AS coding sequence. Expression of the marker in response to induction or selection indicates expression of the plant AS coding sequence. Two marker gene constructs which may be of particular value for monitoring promoter activity in plant cells and plants are the bacterial glucuronidase gene, GUS (Jefferson et al., 1987, EMBO J. 6:3901–3908) or the luciferase gene (Ow et al., 1987, Science, 234:856–859).

In the third approach, transcriptional activity for the plant AS coding region can be assessed by hybridization assays. For example, RNA can be isolated and analyzed by Northern blot using a probe homologous to the plant AS coding sequence or particular portions thereof substantially as shown in FIG. 2. Alternatively, total nucleic acids of the host cell may be extracted and assayed for hybridization to such probes.

In the fourth approach, the expression of the AS protein product can be assessed immunologically, for example by Western blots, immunoassays such as radioimmunoprecipitation, enzyme-linked immunoassays and the like. The ultimate test of the success of the expression system, however, involves the detection of the biologically active plant AS gene product. Where the host cell secretes the gene product, the cell free media obtained from the cultured transfectant host cell may be assayed for plant AS activity. Where the gene product is not secreted, cell lysates may be assayed for such activity. In either case, a number of assays can be used to detect AS activity including but not limited to measuring the conversion of $^{14}$C-aspartate to $^{14}$C-asparagine (Joy et al., 1983, Plant Physiol. 73:165–168, Shelp & Atkins, 1984, Plant Science Letters 36:225–230; Huber & Streeter, 1984, Plant Physiol. 74:605–610; Huber et al., 1985, Plant Sci. 42:9–17); measuring such conversion by absorption (Rognes, 1975, Phytochem. 14:1975–1982; Loyola-Vargas, 1988, J. Plant Physiol. 132:289–293); or measuring AS by HPLC (Unnithan et al., 1984, Anal. Biochem. 136:198–201).

In the fifth approach, the production of a biologically active plant AS gene product can be assessed by the complementation assay, in which an Asn⁻ host transformed or transfected with the AS expression vector is grown on asparagine minus media. The expression of a biologically active holoenzyme is indicated by the growth of such transformants/transfectants in the absence of asparagine. As previously explained, this may be used in conjunction with a separate selectable marker to ensure incorporation of the vector.

In the sixth approach, mutant or wild-type plant AS which is resistant to herbicides can be selected using the complementation assay expression system by exposing the clones which express biologically active AS to various concentrations of different herbicides. Growth in an asparagine minus media in the presence of the herbicide indicates expression of a resistant, active holoenzyme.

Once a clone that produces high levels of biologically active plant AS is identified, the clone may be expanded and used for a variety of ends; e.g., production of plant AS which may be purified using techniques well known in the art including but not limited to immunoaffinity purification, chromatographic methods including high performance liquid chromatography, and the like; screening herbicides; and engineering transgenic plants which are herbicide resistant, salt/drought tolerant and/or pathogen resistant.

5.3. USES OF PLANT ASPARAGINE SYNTHETASE GENE AND GENE PRODUCT

Our studies concerning AS mRNA accumulation have highlighted the importance of the two different AS mRNAs during plant development. The AS cDNA clones can be used to characterize the distinct AS1 and AS2 gene products; to express AS so that antibodies which define AS1 or AS2 gene products can be produced; to screen and develop new herbicides; to develop herbicide resistant plants, salt/drought tolerant plants or pathogen resistant plants; and to aid in the identification of novel cell cycle inhibitors which can be used to synchronize plant cell cultures.

5.3.1. PRODUCTION OF ANTIBODIES THAT DEFINE AND/OR INHIBIT PLANT AS

Expressed gene products may be used to produce antibodies that define AS1 or AS2. These antibodies can be used in organelle fractionation studies to define the subcellular site of action of these distinct AS polypeptides so that previous biochemical studies which report either cytosolic or plastid localization of AS activity in plant cells can be clarified. For full length cDNA clones, the corresponding proteins may be produced in E. coli in sufficient quantities to allow characterization in terms of substrate preference (i.e. ammonia or glutamine), Km, sensitivity to inhibitors, etc.

Such antibodies may be produced by any method known in the art, including, but not limited to injection of plant AS into mice, rats, rabbits, or other host species for production of polyclonal antisera. Various adjuvants may be used to increase the immune response. These include, but are not limited to Freund's (complete and incomplete), mineral gels such as aluminum hydroxide, surface active substances such as lysolecithin, pluronic polyols, polyanions, peptides, and oil emulsions. For a review of such techniques, see Harlow & Lane, 1988, Antibodies A Laboratory Manual, Cold Spring Harbor Laboratory.

Monoclonal antibodies, or fragments thereof, can be prepared by any technique which provides for the production of antibody molecules by continuous cell lines in culture. Such techniques include but are not limited to the hybridoma technique first developed by Kohler and Millstein (1975, Nature 256:495-497), the human B-cell hybridoma technique (Kozbor et al., 1983, Immunology Today 4:72); and the EBV-hybridoma technique for production of human monoclonal antibodies (Cole et al., 1985, Monoclonal Antibodies and Cancer Therapy, Alan R. Liss, Inc., pp. 77-96).

Antibody fragments which contain the idiotype of the molecule could be generated by known techniques. For example, such fragments include but are not limited to: the F(ab')$_2$ fragment which can be produced by pepsin digestion of the antibody molecule; the Fab' fragments which can be generated by reducing the disulfide bridges of the F(ab')$_2$ fragment, and the 2 Fab or Fab fragments which can be generated by treating the antibody molecule with pepsin and a reducing agent.

5.3.2. DEVELOPMENT OF NEW HERBICIDES

AS cDNA clones can be used in functional complementation assays described in Section 5.1, supra, designed to screen for new herbicides as follows. Full length AS cDNAs cloned in the appropriate expression vectors can be introduced into Asn strains of bacteria, algae yeast, neurospora, or higher plant or animal cells as previously described. The ability of an AS cDNA clone to confer asparagine independent growth to the Asn$^-$ mutant cells would indicate that the cDNA encodes an AS polypeptide which is able to assemble into an active holoenzyme in these heterologous environments.

The in vivo complementation experiments will determine whether AS1 and AS2 encode separate subunits of separate holoenzyme complexes or whether they encode two different subunits of a single holoenzyme complex. That a plant enzyme for AS can assemble and function in a heterologous environment is supported by the findings that cDNAs for higher plant GS can functionally rescue GlnA$^-$ strains of E. coli even though the plant and E. coli enzymes differ dramatically (Das Sarma, 1986, Science, 232:1242-1244; Snustad et al., 1988, Genetics Soc. America vol. 120 (4):1112-1124).

The plant AS cDNAs expressed in Asn$^-$ mutants of bacteria, algae, yeast, neurospora, plant cells or animal cells described previously provide an in vivo system to select for novel herbicides which selectively act on AS. To this end, known concentrations of a test substance can be added to the growth media in order to select those substances which inhibit cell growth as an indication of AS inhibitory activity.

5.3.3. DEVELOPMENT OF HERBICIDE RESISTANT PLANTS AND STRESS TOLERANT PLANTS

The in vivo expression system described above could be modified and used to select for mutations in the plant AS structural gene which confer growth resistance to known herbicides or to the new herbicides. Mutations may be introduced into the plant AS cDNA in vivo or in vitro using techniques well known in the art, including, but not limited to, radiation, chemical mutation, site-specific mutations, etc. For example, see Tilghman and Levine, 1987, in Gene Transfer, Kucherlaputi, Ed., Plenum Pub., N.Y., pp. 189-221). Expression vectors containing such altered or mutated plant AS coding sequences can be used in Asn$^-$ hosts in the complementation assay described above to identify clones containing coding sequences that specify and express biologically active, altered plant AS. Clones which produce herbicide resistant plant AS can be selected by growth in the presence of the herbicide. In this way, clones which produce mutant plant AS can be screened for resistance to various herbicides. Some known inhibitors of plant AS which can be tested in this screening system are listed in Table I below.

TABLE I

| INHIBITORS OF PLANT AS | |
|---|---|
| | Inhibition (%) |
| Aspartate Analogues | |
| erythro β-hydroxy-L-aspartate | 65.4 |
| threo β-methyl-L-aspartate | 58.4 |
| erythro β-methyl-L-aspartate | 51.4 |
| meso-diaminosuccinamate | 50.6 |
| 5-bromo-4-oxo-L-norvaline | 49.5 |
| 5-chloro-4-oxo-L-norvaline | 42.1 |
| Glutamine Analogues | |
| L-azaserine | 97.5 |
| L-albizziine | 85.2 |
| DL-homoglutamine | 42.4 |
| S-carbamoyl-L-cysteine | 35.6 |
| 2-hydroxyethyl-L-glutamine | 31.1 |
| N-CBZ-DL-glutamine | 30.5 |
| L-glutamate-γ-methyl ester | 27.2 |
| L-glutamate-γ-ethyl ester | 23.6 |
| γ-methylene-L-glutamine | 20.4 |
| D-glutamine | 14.8 |
| N-acetyl-L-glutamine | 10.2 |
| L-glutamate diamide | 9.1 |
| L-methionine-S-sulphoximine | 8.6 |
| Asparagine Analogues | |
| erythro-β-hydroxy-L-asparagine | 59.5 |
| N-methyl-L-asparagine | 57.6 |
| β-methyl-DL-asparagine | 55.1 |
| N-ethyl-L-asparagine | 47.2 |
| threo β-hydroxy-L-asparagine | 45.2 |
| 2-amino-2-carboxy-L-ethanesulphonamide | 42.5 |
| 5-di azo-4-oxo-L-norvaline | 40.3 |
| N-α-methyl-L-asparagine | 38.8 |

From Lea & Fowden, 1975, Proc. R. Soc. London B. 192:13-26. Aspartate, glutamine or asparagine analogues were added to the standard $^{14}$C-aspartate conversion assay mixtures at 2 mM, 5 mM and 2 mM, respectively. The reaction rate in the absence of any analogue was taken as zero inhibition.

Plants may then be engineered for resistance to herbicides using appropriate constructs containing the mutated AS genes which encode resistant AS products as defined above. Alternatively, plants may be engineered for resistance to herbicides by the over-expression of wild-type AS. In either case, such transgenic plants may be constructed using methods well known to those skilled in the art including but not limited to techniques involving the use of the Ti plasmids (e.g., *Agrobacterium rhizogenes*), plant viruses, electroporation, direct transformation, microinjection, etc. By way of example, and not by way of limitation, the binary Ti vector system could readily be used to this end (Bevan, 1984, Nuc. Acids Res. 12:8711-8721). This vector contains a selectable marker, neomycin phosphotransferase (kanR), under direction of the nopaline synthetase promoter (nos) for KanR selection in plants, and unique cloning sites for EcoRI, HindIII, BamHI, Sma, Sal, Kpn, Kba, SstI. Using this system, DNA fragments cloned into one of the unique cloning sites located between the left and right T-DNA borders are transferred into dicot plants when introduced into *Agrobacterium tumefaciens* LB4404 harboring a resident diarmed Ti plasmid which will provide vir gene required for T-DNA transfer in trans. Another vector system which could be used is the pMON505 intermediate binary Ti transformation vector (Horsch & Klee, 1986, Proc. Natl. Acad. Sci. 83, 4428-4432; Horsch et al., 1985 Science, 227:1229-1231). For reviews of such techniques see, for example, Weissbach & Weissbach, 1988, Methods for Plant Molecular Biology, Academic Press, N.Y., Section VIII, pp. 421-463; and Grierson & Corey, 1988, Plant Molecular Biology, 2d Ed., Blackie, London, Ch. 7-9. AS genes altered in vivo or in vitro to overproduce wild type AS or herbicide resistant forms of AS enzymes may be used as dominant selectable markers for transformation systems which include organisms such as bacteria, algae, yeast, neurospora, plants and animal cells.

By way of illustration, herbicide resistant plants can be engineered in at least two ways: AS cDNAs which contain mutations conferring herbicide resistance as measured in the screening assay above, can be introduced into transgenic plants under the transcriptional regulation of a strong constitutive promoter (e.g., 35S promoter of CaMV) or an inducible promoter (e.g., the promoter of the small subunit of RUBISCO; a heat shock promoter, etc.). Mutant AS produced in the transgenic plants will assemble with wild-type subunits to confer resistance. Alternatively, herbicide resistant plants could be developed by the over-expression of the wild-type AS cDNA. The over-expression of AS in these transgenic plants will produce plants resistant to high levels of a herbicide specific for AS. While overexpression of other amino acid biosynthetic genes may be detrimental to plant metabolism, the over-expression of AS will not harm plant metabolism since asparagine is an ideal nitrogen storage compound, and may in fact actually benefit the plants in ways other than herbicide resistance.

The overexpression of wild-type or mutant AS in transgenic plants may confer resistance or tolerance to salt, drought and/or pathogens. Asparagine has been shown to accumulate in a variety of conditions in plants in response to stress. For example, asparagine and proline accumulate in leaves of water-stressed plants and are thought to serve to help maintain osmotic conditions. Free asparagine has also been shown to accumulate in plants under growth conditions of sulfur starvation (Baudet et al., 1986, Physiol. Plant 68(4):608-614); increased salinity (Chen et al., 1988, Plant Physiol. 86 (4 Suppl.):56 (Abstr); Jeschke et al., 1986, J. Plant Physiol. 124: 257-274); drought (Drossopoulos et al., 1985, Ann. Bot. London 56: 291-306; Fukutoku & Yamada, 1984, Physiol. Plant 61:622-268) and also in plants infected with plant pathogens (Walters & Ayres, 1980, Physiol. Plant Pathol. 17:369-380). The over-production of asparagine in these contexts may endow the transgenic plants with a protective mechanisms that enables them to grow better than wild type. It has recently been shown in alfalfa plants coinfected with the pathogen *P. syringae* and the symbiont *R. meliloti*, that although GS activity is severely inhibited by toxin (Tabtoxinine $\beta$-lactam) produced by *P. syringae*, the infected alfalfa plants assimilate greater total amounts of nitrogen than their counterpart controls. This finding suggests that alternate routes of ammonia assimilation (i.e., asparagine synthetase) can occur in plants which confer better growth properties to a plant (Knight & Langston-Unkefer, 1988, Science 241:951-952).

5.3.4. IDENTIFICATION OF AGENTS THAT SYNCHRONIZE PLANT CELLS IN CULTURE

The screening assay described above could also be used to identify AS inhibitors that could be tested as cell cycle inhibitors useful for synchronizing plant cells in culture. It has been shown in yeast that mutations in amino acid biosynthesis enzymes demonstrate cell cycle defects (Wolfner et al., 1975, J. Mol. Biol. 96:273-290). It has been shown that cell cycle mutants in mammals are deficient in asparagine synthetase (Greco et al., 1987, Proc. Natl. Acad. Sci. 84:1565-1569). By analogy, inhibitors of AS defined by the foregoing screening system could be tested as cell cycle inhibitors to arrest growth of cells in culture, and therefore, synchronize cells in culture. This may have wide applicability to the production of man compounds in cell culture in industry.

In another embodiment, AS genes altered in vivo or in vitro to encode altered forms of AS could be introduced into a cell line under transcriptional direction of an inducible promoter. Induced expression of altered AS would arrest cells within the cell cycle and act to synchronize the cell culture.

5.4. THE PLANT ASPARAGINE SYNTHETASE PROMOTER

As described above and exemplified below, the AS promoter directs high levels of expression in nitrogen fixing root nodules in cotyledons of germinating seeds, and dark-induced gene expression in leaves. This promoter can be used to direct the regulated expression of heterologous gene sequences in appropriate hosts. Another promoter which exhibits photophobic transcription is the promoter of the rice phytochrome gene (Hersey et al., 1985, Nuc. Acids Res. 13:8543-8559; Hershey et al., 1987, Gene 61:339-348; Kay et of transcription are not achieved with the phytochrome promoter. By contrast, the plant AS promoter described herein is not only inducible by darkness, but drives high levels of transcription.

The nucleotide sequence of the plant AS1 promoter is shown in FIG. 10, and the nucleotide sequence for the plant AS2 promoter is shown in FIG. 12. Conserved DNA sequences of the plant AS1 and AS2 promoters are shown in FIG. 13.

The organ-specific and photophobic promoters can be used in a variety of DNA vectors to drive the expression of heterologous sequences ligated after the transcription start site indicated by an arrow in FIG. 10 and upstream from the arrow shown in FIG. 12. Heterologous sequences ligated downstream of the transcription start site, containing a portion of the leader sequence, will require translational control elements such as the ATG start signal, and ribosome binding sites etc. Optionally, the heterologous sequences may also be ligated in a translational fusion to marker genes such β-galactosidase, GUS, luciferase, etc. to produce fusion proteins.

Such expression vectors may be used in plant cell culture or in transgenic plants to direct high level expression of the heterologous sequence in an inducible, temporal, or organ-specific fashion.

As demonstrated by the examples described infra, isolated AS1 promoter was able to direct the expression of a GUS reporter gene in leaves of dark-grown transgenic tobacco plants (see FIG. 11). Results of in situ GUS stained leaves reveals that the AS1 promoter directs GUS expression specifically in the phloem cells. Deletion analysis revealed that the DNA sequences important for AS1 promoter function are contained within a 569 bp fragment of the AS1 promoter (see FIG. 11).

The AS2 promoter shares nucleotide homology with AS1 within the region of the AS1 promoter required for gene expression. These conserved DNA sequence elements (FIG. 13) may correspond to cis-acting DNA elements responsible for AS1 and AS2 gene expression.

6. EXAMPLE: cDNA CLONING OF PLANT ASPARAGINE SYNTHETASE

The following subsections describe the genomic cloning and cDNA cloning of plant AS from pea cDNA and genomic libraries. Briefly, human AS cDNA was used to screen a pea nodule cDNA library in order to isolate AS1 cDNA clones by heterologous hybridization. Coding regions of the AS1 cDNA were then utilized to screen a pea genomic library, resulting in the isolation of AS1 and AS2 genomic clones. The AS2 genomic clones were then utilized to screen a pea root cDNA library in order to isolate AS2 cDNA clones.

6.1. MATERIALS AND METHODS

Seeds of *P. sativum* (var. "Sparkle") obtained from Rogers Brother Seed Co. (Twin Falls, Id.) were imbibed and germinated in a Conviron environmental chamber with a day length of 16 hours, illumination of 1000 microeinsteins/m$^2$/s [1 einstein (E)=1 mol of photons], at a day/night cycle of 21°/18° C. For etiolated plants, peas were grown for 7-9 days in black lucite boxes contained in a dark environmental chamber. For germination studies, seeds were imbibed in water and germinated in vermiculite. Nodules were isolated from 21 day old pea plants inoculated with *Rhizobium leguminosum* strain 128C53 (Nitragin Co., Milwaukee, Wis.) as described previously (Tingey et all, 1987, EMBO J. 6:1-9).

For phytochrome induction experiments, 9 day old etiolated pea seedlings were irradiated with a 4 minute pulse of red light (red fluorescent lamps, General Electric F20T12R) at a fluence of 40 μE/m$^2$/s or were given a 4 minute pulse of red light followed by 12 minutes of far-red light (Westlake, FRF700) at the same fluence and were then returned to the dark for 3 hours. For white light treatment, etiolated seedlings were exposed to continuous white light for 8 hours.

The subsections below describe the methods used to isolate and prepare the AS genomic and cDNA clones from the pea libraries. The pea cDNA libraries used are described in Tingey et al, 1987, EMBO J. 6:1-9, which is incorporated by reference herein in its entirety.

6.1.1. ISOLATION OF PLANT AS1 cDNAs

AS cDNA clones were selected from a pea nodule cDNA library from *Pisum sativum* (var. "Sparkle") in λgt11 (Tingey et al., 1987, EMBO J. 6:1-9) as follows. Nitrocellulose filters containing denatured phage DNA corresponding to 250,000 individual plaques were incubated for 4 hours at 45° C. in prehybridization buffer (6×SSC 10×Denhardt's Solution, 0.1% SDS, 1 mM EDTA, 100 μg/ml denatured salmon sperm DNA). Filters were then incubated for 24 hours at 45° C. in hybridization buffer (6×SSC, 5×Denhardt's Solution, 0.1% SDS, 1 mM EDTA, 50 μg/ml denatured salmon sperm DNA) plus 0.2 μg of $^{32}$P labeled cDNA insert (a 1.7 kb Hind III fragment) of pH131 (Andrulis et al., 1987, Mol. Cell Biol. 7:2435-2443). The DNA probe was made radioactive with α-$^{32}$P nucleotide by the random priming method (Feinberg & Vogelstein, 1983, Anal. Biochem. 132: 6; Ibid 137:266) to a specific activity of 2×10$^8$ cpm/μg. Filters were washed in 1×SSC, 0.1% SDS for 15 minutes at room temperature, followed by 15 minutes at 45° C. Filters were exposed to X-ray film for 24 hours. AS cDNA clones, λcAS301 and λcAS305 (FIG. 1A), isolated via heterologous hybridization to the human AS probe (pH131), were purified via three rounds of plaque purification and DNA prepared according to Maniatis et al., 1982, Molecular Cloning A Laboratory Manual, Cold Spring Harbor Laboratory, pp. 63-67, and 76-85. Restriction fragments of λcAS301 (FIG. 1A, 1373 bp SstI/BamHI fragment "b") and λcAS305 (FIG. 1A, 423 bp BamHI/EcoRI fragment "c") were subcloned into pTZ18U or pTZ19U (Genescribe TM, U.S. Biochemical Corp., Cleveland, Ohio). For further sequence analysis, restriction fragments were subcloned into M13mp18 or M13mp19 (Yanisch-Perron, et al., 1985, Gene 33:103-119; Biggin et al.,.1983, Proc. Natl. Acad. Sci. (USA) 80:3963-3965).

6.1.2. SYNTHESIS OF FULL LENGTH AS1 cDNA cDNA clones corresponding to the 5, end of AS1 mRNA (i.e. λcAS907) were synthesized using the following 40 base oligonucleotide primer complementary to the 5' end of λcAS301 (in which "nt" numbers refer to the complementary nucleotide positions within the full length sequence shown in FIG. 2A):

```
              10         20        30       40
5'-CCAGCAAGGTATCTAGCAGTGACAGACGCGACCAACGATG-3
848nt                                          809nt
```

This 40 base oligonucleotide was annealed with 5 μg pea nodule polyadenylated RNA. First strand synthesis was performed using reverse transcriptase according to Verma, 1981, in, The Enzymes: Nucleic Acids Part A, XIV, Boyer Ed., Acad. Press, N.Y., pp. 87-103 as described (BRL cDNA Synthesis System, Catalog No. 8267SA). Following second strand synthesis, EcoRI linkers were added (Maniatis et al., 1982, Molecular Cloning A Laboratory Manual, Cold Spring Harbor Laboratory, pp. 243-246) and the cDNA fragments were ligated into Lambda ZAP ®II vector (Stratagene, La Jolla, Calif.). cDNA inserts were subcloned into M13mp18 and M13mp19 and analyzed by DNA sequence analysis (Biggin et al., 1983, Proc. Natl. Acad. Sci. (USA) 80:3963-3965). The full length cDNA clone, pcAS1 (2135bp), encoding AS1 was constructed from the sequential ligation of the 423 bp BamHI/EcoRI fragment of λcAS305 (FIG. 1A, fragment "c"), the 1373 bp SstII/BamHI fragment of λcAS301 (FIG. 1A, fragment "b"), and the 339 bp EcoRI/SstII fragment of pcAS907 (FIG. 1A, fragment "a") into the EcoRI site of pTZ18U (Genescribe ™, U.S. Biochemical Corp., Cleveland, Ohio) as shown in FIG. 1A. The resulting clone, designated pTZ18U/cAS1 (or pcAS1) was deposited with the NRRL as described infra.

6.1.3. ISOLATION OF PLANT AS GENOMIC CLONES

Using the techniques described above, AS1 and AS2 genomic clones were isolated from Pisum sativum (var. "Feltham First" genomic library constructed in λ EMBL 3 (Frischauf et al., 1983, J. Mol. Biol. 170:827-842) using size fractionated partial digests of Sau3A cleaved leaf DNA amplified in E. coli K803 and screened on the selective lysogen Q359 (Lycett et al., 1985, Nuc. Acids Res. 13:6733-6743). This genomic library was probed with a portion of the coding region of the AS1 cDNA (fragment "b" in FIG. 1A). Two clones were identified and isolated, μgAS1 which hybridized strongly to the AS1 cDNA probe, and λgAS2 which hybridized more weakly to the AS1 cDNA probe (see FIG. 1C). A 3.2 kb SstI/BamHI fragment of λgAS1 was subcloned into pTZ18U resulting in pgAS1.a, and a 5.5 kb BamHI fragment of λgAS2 was subcloned into pTZ18U resulting in pgAS2.a as shown in FIG. 1C. Both genomic clones, pgAS1.a and pgAS2.a were deposited with the NRRL as described infra. Fragments were subcloned into M13mp18 and M13mp19 for sequence analysis shown in FIG. 2C.

6.1.4. ISOLATION OF PLANT AS2 cDNAs

The genomic clone λgAS2 was used to isolate AS2 cDNA as follows. A 1.5kb EcoRI/BamHI fragment of AS2 genomic clone, λgAS2, containing 3' noncoding region and some of the AS2 coding region (FIG. 1C) was used to screen a pea root cDNA library (Tingey et al., 1987, EMBO J. 6:1-9) to isolate AS2 cDNA clones. The pea root cDNA library was used for this purpose because Northern analyses revealed that in the root, AS2 expression is higher than that of AS1. The cDNA clone containing the longest insert, pcAS2-01 (FIG. 1B), was isolated and subcloned into the EcoRI site of pTZ19U (Genescribe ™ U.S Biochemical Corp., Cleveland, Ohio), resulting in cDNA clone pTZ19U/cAS2-01 (or pcAS2-01) which was deposited with the NRRL as described infra.

The cDNA clones containing the 5' end of AS2 mRNA were amplified from pea nodule poly(A)+ RNA by anchored polymerase chain reaction (A-PCR) technique (Loh et al. 1989, Science 243:217-220). First strand cDNA was synthesized in a reaction mix containing 50 mM Tris-HCl, pH 8.3, 75 mM KCl, 3 mM MgCl$_2$, 50 mM dithiothreitol, 0.5 mM dNTP, 5 μg nodule poly(A)+ RNA, 200 U M-MLV reverse trancriptase (Bethesda Research Labs, Gaithersburg, Md.) and 1 μg oligonucleotide FY13 (5'-GGCCGAATTCATACAAATGACCAGGTGGAAAACAC) which includes an EcoRI site plus sequences complementary to the 5' end of cAS201 (617-641 nt, see FIG. 2B) at 37° C. for 1 hour. The reaction was stopped by phenolchloroform extraction and the supernatant was passed through Linker 6 Quick Spin ™ Columns (Boehringer Mannheim Biochemicals, Indianapolis, Ind.) to remove excess linkers. After ethanol precipitation, the tailing reaction was performed according to manufacturer's instructions in 50 μl of reaction mix containing 20 μM of dGTP, 1×TdT buffer and 15 U of terminal deoxynucleotidyl transferase (TdT) (Bethesda Research Labs) at 37° C. for 30 minutes. After phenol-chloroform extraction and ethanol precipitation, the tailed cDNAs were redissolved in 20 μl of water and used as templates in an A-PCR reaction. The A-PCR reaction was performed with Taq polymerase (Perkin-Elmer Cetus, Norwalk, Conn.) in 100 μl of a buffer containing 5 μl of the tailed cDNAs, 0.1 mM of dNTP, 2.5 μg of AS2 specific primer (FY13) and 2.5 μg of an anchored primer mix containing a 1:9 ratio of AnC primer (5'-CAGGTCGACTCTAGAGGATCCCCCCCCCCCCCCC) and An primer (5'-CAGGTCGACTCTAGAGGATCCC). A program of six cycles of low-stringency hybridization and amplification (94° C. for 45 seconds followed by annealing at 37° C. for 1 minute and elongation at 72° C. for 2 minutes) was followed by 24 cycles of high-stringency hybridization and amplification (94° C. for 45 seconds followed by annealing at 55° C. for 1 minute and elongation at 72° C. for 2 minutes). The amplified cDNAs were precipitated by ethanol, digested with EcoRI and BamHI, then separated on an agarose gel. A predominant DNA fragment of about 600 bp was recovered from the agarose gel and ligated into the EcoRI and BamHI sites of pTZ19U (Genescribe). The ligated DNA was introduced into E. coli XL1 blue. Clones containing AS2 sequences were isolated and sequenced by the dideoxy method.

6.1.5. DNA AND RNA ANALYSES

Nuclear DNA from Pisum sativum was analyzed by Southern blot analysis according to the method described in Tingey et al., 1987, EMBO J. 6:1-9. Briefly, pea nuclear DNA was digested with SstI, EcoRI, BamHI or HindIII. The fragments resulting from each digest were resolved by gel electrophoresis, transferred to nitrocellulose and probed with a 1373 bp SstI/BamHI $^{32}$P-labeled fragment of AS1 (FIG. 1A, fragment "b") or an 872 bp BamHI/EcoRI $^{32}$P-labeled fragment of AS2 (FIG. 1B, 3' end of pcAS2-01). The genomic Southern blot was performed at high stringency (hybridized at 70° C. and washed at 70° C. in 0.1×SSC and 0.1% SDS) such that cAS1 and cAS2 cannot cross-hybridize to each other.

Northern analyses of mRNA obtained from leaves, roots, nodules or cotyledons of Pisum sativum were performed according to the method described by Tingey et al., 1987, EMBO J. 6:1-9. Briefly, the total RNA or polyadenlyated RNA obtained was denatured, resolved by gel electrophoresis, transferred to nitrocellulose and probed with a 423 bp BamHI/EcoRI $^{32}$P-labeled fragment of AS1 (FIG. 1A, fragment "c") or a 224 bp HincII/EcoRI $^{32}$P-labeled fragment of AS2 (FIG. 1B, 3' end of pcAS2-01), which have specific activities of about $1-2\times10^8$ c.p.m./μg. The intensities of gene-specific mRNA were determined by densitometer. For Northern blot analysis in which poly(A)+ RNA was used, the quantitations were standardized using β-subunit of mitochondrial ATPase mRNA as a control. Sizes of mRNAs were estimated by migration relative to denatured DNA markers.

6.2. RESULTS

6.2.1. ISOLATION OF TWO CLASSES OF PEA AS cDNA CLONES cDNA clones encoding plant AS were selected from the pea nodule cDNA library (Tingey et al., 1987, EMBO J. 6:1-9) by hybridization to a heterologous DNA probe encoding human asparagine synthetase (Andrulis et al., 1987, Mol. Cell Biol. 7:2435-2443). From 50 positive clones identified out of $2 \times 10^5$ clones screened, eight clones (λcAS301-λcAS308) were randomly selected for further analysis. Restriction mapping and nucleotide sequence analysis of these clones revealed that all eight contained cDNA inserts which correspond to overlapping portions of a single mRNA species, AS1 (FIG. 1A). A cDNA clone (λcAS907) containing the 5' end of the AS1 mRNA was synthesized using an oligonucleotide derived from the 5' end of λcAS301. The restriction maps of three overlapping cDNA clones which include the entire AS1 coding region are shown in FIG. 1A. Restriction fragments of the three overlapping cDNA clones (λcAS907, λcAS301, and λcAS305) were ligated to form the composite full length 2.2 kb cDNA clone called pcAS1 (FIG. 1A).

A second type of AS coding sequence (AS2) was detected in peas when a DNA fragment from the coding region of an AS1 cDNA was used to screen a pea genomic library. cDNA clones encoding the AS2 mRNA were subsequently isolated from a pea root cDNA library using an AS2 genomic fragment as a DNA probe. The longest AS2 cDNA clone, λcAS201, which contains a 1.5 kb cDNA insert, was selected for further analysis (FIG. 1B). A cDNA containing the 5' end of the AS2 mRNA (pcAS801) was synthesized in vitro by anchored polymerase chain reaction (A-PCR) using an oligonucleotide primer complementary to the 5' end of λcAS201 as described above. The restriction map of the full length cDNA of AS2 (cAS2) was deduced from the overlapping partial cDNA clones λcAS201 and pcAS801.

6.2.2. pcAS1 AND cAS2 REPRESENT HOMOLOGOUS AS mRNAs WHICH ENCODE DISTINCT AS POLYPEPTIDES

The nucleotide sequences of the full-length AS1 and AS2 cDNAs are shown in FIG. 2. pcAS1 is 2200 nt long, and starting with the first in-frame methionine, encodes a protein of 586 amino acids with a predicted molecular weight of 66.3 kd. The 3' non-coding region of AS1 cDNA is 333 nt long and contains a poly(A) tail (FIG. 2A). cAS2 is 2002 nt long and encodes a protein of 583 amino acids with a predicted molecular weight of 65.6 kd. The 3' non-coding region of cAS2 is 141 nt long and contains a poly(A) tail (FIG. 2B).

As shown in FIG. 3 and Table II, the nucleotide sequence homology between cDNAs corresponding to AS1 and AS2 mRNA is 81%. This homology is confined to the protein coding regions of the two cDNAs, whereas there is no significant homology in the 3' non-coding regions of these cDNAs. Due to the degeneracy of the universal code, the cDNAs for AS1 and AS2 are even more homologous when encoded amino acids are compared 86%). The overall nucleotide homology between either AS cDNA of pea and the AS cDNA of human is about 50 to 55% within the coding regions. Neither pea AS cDNA shares significant homology to the AS gene of *E. coli* (Nakamura et al., 1981, Nucleic Acids Res. 9:4669-4676).

TABLE II

| | Percent Homology of Plant AS and Human AS* | | | | | | |
|---|---|---|---|---|---|---|---|
| | % Nucleotide Homology | | | | % Amino Acid Homology | | |
| | AS1 | AS2 | pH131 | | AS2 | AS2 | pH131 |
| AS1 | 100% | 81% | 50% | AS1 | 100% | 86% | 47% |
| AS2 | 81% | 100% | 55% | AS2 | 86% | 100% | 47% |
| pH131 | — | — | 100% | pH131 | — | — | 100% |

*AS1 and AS2 encode plant AS. pH131 is a full length cDNA clone encoding human AS (Andrulis et al., 1987, supra). Nucleotide and amino acid homologies were determined using the "fasta" computer program (Lipman & Pearson, 1985, Science 227:1427; Pearson & Lipman, 1985, Proc. Natl. Acad. Sci. (USA) 85:2444).

That the pea cDNA clones for AS1 and AS2 encode plant AS was confirmed by a comparison of their encoded amino acids to those deduced for human AS as shown in FIG. 3. The polypeptides encoded by the pea AS1 and AS2 cDNAs share an overall homology of 86% at the amino acid level. A comparison of the pea AS and human AS polypeptides reveals an overall homology of 47% which extends along the entire AS polypeptide (Table II). There are several regions of high local homology (greater than 80%) shared between the pea AS and human AS polypeptides (amino acid residues 116-128; 218-243; 340-348; 352-360; 392-401; and 486-500 in the pea AS1 protein). In particular, the first four amino acids of the human AS protein (Met-Cys-Gly-Ile), which have been shown to be the glutamine binding site (Heeke and Schuster, 1989, J. Biol. Chem. 264:5503-5509) are perfectly conserved in both the pea AS1 and AS2 proteins. A region of divergence between the pea AS and human AS proteins occurs at amino acid residues 165-234 of the human AS protein. This stretch of amino acids is not found in either pea AS1 or AS2 polypeptide and may be the result of gene modification (deletion or insertion) during evolution of plant versus animal AS.

6.2.3. AS1 AND AS2 ARE ENCODED BY SINGLE NUCLEAR GENES IN THE PEA GENOME

Southern blot analysis of nuclear DNA was used to examine the number of genes encoding AS in *Pisum sativum* (FIG. 4). Southern blots probed with a DNA probe from the coding region of pcAS1 as described, detect a single genomic fragment in each of the four restriction digests (FIG. 4A, lanes 1-4). Replicate blots probed with a DNA probe from the coding region of the pcAS201 cDNA reveal that AS2 is also present as a single gene (FIG. 4B, lanes 5-8). The results shown in FIG. 4 reveal that in each digestion only a single genomic DNA restriction fragment hybridizes to each probe. In addition, the genomic DNA fragments which hybridize to either AS1 or AS2 cDNA probes are distinct. Similar results were obtained with DNA fragments containing 3' non-coding sequences of pcAS1 or cAS2. These results indicate that peas contain a single gene for AS1 and a distinct single gene for AS2.

6.2.4. PHOTOPHOBIC ACCUMULATION OF AS1 mRNA IN LEAVES

Previous biochemical studies have shown that AS enzyme activity increases when plants are grown in the dark (Joy et al., 1983, Plant Physiol. 73:165-168). To address whether this increase in AS enzyme activity reflects an increase in AS gene expression in the dark, gene-specific probes derived from 3' non-coding regions of AS1 and AS2 cDNAs were used in Northern blot experiments to detect AS mRNAs in leaves of plants grown under different light regimes (FIG. 5). AS1 mRNA (2.2 kb) accumulates to high levels in leaves of mature dark-adapted green plants (FIG. 5A, lanes 2 and 3). However, when these plants are transferred to continuous white light, the steady-state levels of AS1 mRNA decrease dramatically to almost undetectable levels (FIG. 5A, lanes 4 and 5). In mature plants, both the dark-induced and light-repressed accumulation of AS1 mRNA can be detected 6 hours after changing the light conditions (FIG. 5A, lanes 2 and 4 respectively). The steady-state levels of AS1 mRNA in leaves of dark-adapted plants (FIG. 5A, lane 3) are 30-fold higher than the AS1 mRNA levels present in leaves of light-grown plants (FIG. 5A, lane 5). As a control, mRNA for cytosolic GS (1.4 kb) monitored on the same blot revealed no dramatic changes in mRNA levels in response to the light treatments. AS2 mRNA levels were also detected on replicate blots with a DNA probe from the 3' non-coding region of cAS2. These experiments revealed that AS2 mRNA (2.2 kb) is present at much lower levels than AS1 mRNA in leaves of dark-grown plants and is undetectable in leaves of grown plants.

Northern blots were also performed on RNA isolated from plants at various developmental stages which were grown in continuous white light (FIG. 5B, lanes 1, 3, 5 and 7) and then transferred to the dark (FIG. 5B, lanes 2, 4, 6 and 8). The results of these experiments reveal that the dark-induced accumulation of AS1 occurs in plants of all developmental stages but is most dramatic in mature plants. The dark-induced increase of AS1 mRNA varies from 5-fold in 10 day old plants (FIG. 5B, compare lanes 1 and 2) to greater than 20-fold in 31 day old plants (FIG. 5B, compare lanes 7 and 8). As a control, Northern blots reprobed with a DNA probe encoding a cytosolic form of glutamine synthetase, GS (Tingey et al., 1988, J. Biol. Chem. 263:9651-9657, which is incorporated by reference herein in its entirety) reveal that the mRNA for cytosolic GS (1.4 kb) is relatively unaffected by the different light treatments (FIG. 5B, lower band).

AS1 mRNA (2.2 kb) is expressed at high levels in leaves of dark-grown or dark-adapted plants (FIG. 5C, lane 1, and FIG. 5D lane 2, respectively). AS1 mRNA levels decrease dramatically when these plants are transferred to continuous white light (FIG. 5C, lane 2, and FIG. 5D, lane 3). This "photophobic" nature of AS1 mRNA accumulation is also evident in mature light-grown pea plants (FIG. 5D lane 1). The photophobic accumulation of AS1 mRNA in the dark is in direct contrast to the light-induced accumulation of the 1.5 kb mRNA for chloroplast GS2 (Tingey et al., 1988, J. Biol. Chem. 263:9651-9657); see FIGS. 5C and 5D, lower molecular weight signal. AS2 mRNA is present at relatively low levels in leaves of dark- or light-grown plants. It is noteworthy that the photophobic accumulation of AS1 mRNA in leaves of plants transferred to darkness occurs in plants at various stages of development (FIG. 5B). The mRNA for cytosolic GS (1.4 kb) is unaffected by the light treatments (FIG. 5B, lower molecular weight signal).

In order to determine whether the plant photoreceptor phytochrome is involved in mediating the dark-induced expression of AS1 gene in peas, AS1 mRNA was examined in etiolated plants treated with light regimes known to activate or inactivate phytochrome (FIG. 5E). While AS1 mRNA accumulates to high levels in etiolated plants (FIG. 5E, lane 1) the levels of AS1 mRNA decrease dramatically in plants treated with a red-light pulse (FIG. 5E, lane 2). The repression of AS1 expression by red light is partially reversed by a subsequent pulse of far-red light (FIG. 5E, lane 3). The effects of red and far-red light pulses on accumulation of AS1 mRNA were detected within 3 hours after light treatment. These results show that the dark-induced accumulation of AS1 mRNA is mediated, at least in part, through the chromophore phytochrome.

6.2.5. BOTH AS1 AND AS2 mRNAs ARE EXPRESSED AT HIGH LEVELS DURING DEVELOPMENTAL CONTEXTS INVOLVING INCREASED NITROGEN TRANSPORT

To determine whether the level of AS mRNA increases in contexts where large amounts of asparagine are synthesized for nitrogen transport, the steady-state levels of AS1 and AS2 mRNAs were monitored in nitrogen-fixing root nodules of peas and in cotyledons of germinating pea seedlings (FIG. 6). Asparagine serves as a major nitrogen transport amino acid during germination. The results of the gene-specific Northern blots for AS reveals that both AS1 and AS2 mRNAs accumulate to high levels in cotyledons of germinating pea seedlings (FIG. 6A). While AS1 mRNA can be detected after 10 days of germination (FIG. 6A, lane 5' panel), AS2 mRNA is detected earlier (4-6 days of germination) (FIG. 6A, lanes 2 and 3' lower panel). There is a greater than 20-fold increase of both AS1 and AS2 mRNAs in cotyledons during germination time course (FIG. 6A, compare lanes 2 and 7). The same Northern blot reprobed with DNA probe for a cytosolic form of glutamine synthetase, GS (Tingey et al., 1988, J. Biol. Chem. 263:9651-9657), reveals that mRNA for cytosolic GS accumulates earlier (2-4 days) than either AS mRNA.

AS mRNA levels were also examined in nitrogen-fixing root nodules of pea where asparagine serves as a major compound for nitrogen transport from nodules to the rest of the plant. RNA from nitrogen-fixing root nodules and roots of uninfected plants were probed in Northern blot experiments with gene-specific AS probes (FIG. 6B). These experiments reveal that both AS1 and AS2 mRNAs accumulate to very high levels in nitrogen-fixing nodules (FIG. 6B, lane 2) compared to uninfected roots (FIG. 6B, lane 1). The induction of AS1 mRNA in nodules compared to roots is 20-fold while that of AS2 mRNAs is only 5-fold. The lower fold induction of AS2 mRNA may reflect the higher basal levels present in uninfected roots (FIG. 6B, lane 1). As a control, the Northern blot was reprobed with a DNA probe for the $\beta$-subunit of the mitochondrial ATPase (Boutry and Chua, 1985, EMBO J. 4:2159-2165) which is expressed at equal levels in roots of uninfected plants and nitrogen-fixing nodules (FIG. 6B, lower panel).

6.3. DISCUSSION

While asparagine is an important nitrogen transport amino acid in higher plants, the enyzme involved in its synthesis is poorly characterized to date due to enzyme instability in vitro. In the examples described, supra, plant AS cDNAs were cloned using a heterologous DNA probe encoding human AS. Two classes of AS cDNAs (AS1 and AS2) that encode homologous but distinct AS proteins were obtained from pea cDNA libraries. The homologies between the pea AS1 and AS2 cDNAs are 81 and 86% at nucleotide and amino acid levels respectively. Full-length cDNAs for AS1 and AS2 of pea were shown to encode proteins whose sizes and amino acid sequences are in excellent agreement with that deduced for the human AS protein. The pea AS1 and AS2 cDNAs and human AS cDNA share an overall nucleotide homology of 50-55% along their entire coding sequence. Regions that are highly conserved between the pea AS and human AS polypeptides (greater than 80% at amino acid level) may likely include important sites for enzyme activity. For example, the first four amino acids in the human AS protein (Met-Cys-Gly-Ile), which have been shown to be the glutamine-binding site and important for enzyme activity (Andrulis et al 1987, Mol. Cell. Biol. 7:2435-2443; Heeke and Schuster, 1989, J. Biol. Chem. 264:5503-5509) are perfectly conserved in both the pea AS1 and AS2 proteins. The degree of sequence homology between the pea AS and human AS proteins supports the conclusion that the full length AS1 and AS2 cDNAs encode glutamine-dependent AS of peas.

The significance of two homologous but distinct AS polypeptides in plants is intriguing. The AS1 and AS2 cDNAs of pea may encode two distinct subunits of a single AS holoenzyme (heterologous holoenzyme); or each subunit may assemble into a separate AS holoenzyme (homologous holoenzyme of either AS1 or AS2 subunits). These two possibilities are not mutually exclusive. Partially purified plant AS enzyme preparations have been shown to utilize glutamine as a preferred substrate; however, ammonia can also be used as a substrate in the same preparations albeit with higher $K_m$ values (Scott et al., 1976, Nature 263:703-705; Huber et al., 1984, Plant Physiol. 74:605-610; 1985, Plant Sci. 42:9-17. The existence of glutamine binding sites at the amino terminus of the pea AS1 and AS2 proteins implies that both AS1 and AS2 genes encode glutamine-dependent forms of AS. It is possible, however, that these AS enzymes are able to utilize ammonia as a substrate in vivo under conditions of ammonia excess. It is interesting to note that glutamine versus ammonia-dependent forms of AS are encoded by separated genes in E. coli (Felton et al., 1980, J. Bacteriol. 142 221-228; Humbert et al., 1980, J. Bacteriol. 142:212-220) and yeast (Jones, 1978, J. Bacteriol. 134:200-207; Ramos et al., 1980, Euro. J. Biochem. 108:373-377). Therefore, we cannot exclude the possibility that plants might contain another distinct AS gene for ammonia-dependent form of AS. Previous biochemical studies have also shown that AS activity can be detected in both soluble and proplastid fractions of nitrogen-fixing nodules of soybean (Boland et al., 1982, Planta 155:45-57). The proteins encoded by AS1 and AS2 cDNAs of pea are most likely cytosolic AS since neither of them contains a transit peptide. It is possible that peas contain another distinct gene for plastid AS.

Northern blot analysis has revealed that the steady-state levels of AS1 and AS2 mRNAs parallel asparagine synthesis in various developmental contexts. For example, previous physiological studies have shown that asparagine is the major nitrogen transport amino acid in plants grown in the dark (Urquhart et al., 1981, Plant Physiol. 68:750-754) and that AS activity can be enhanced by dark treatment (Joy et al. 1983, Plant Physiol. 73:165-168). The experiments described herein demonstrate that in peas the increase of AS activity in the dark is due, at least in part, to an increase in the steady-state levels of AS1 mRNA. This dark-induced accumulation of AS1 mRNA occurs in leaves of both etiolated seedlings and in mature dark-adapted green plants. Moreover, the magnitude of dark-induced AS1 mRNA accumulation increases significantly during plant development. Kinetic experiments reveal that both dark-induced and light-repressed changes in AS1 mRNA levels can be detected within 3 hours in etiolated seedlings (FIG. 5E) and mature plants after changing the light/dark conditions. Thus, the dark-induced accumulation of AS1 mRNA is physiologically significant for plants grown in a short dark period (e.g. at night).

The dark-induced accumulation of the AS1 mRNA classifies the AS1 gene with other genes that are negatively regulated by light such as phytochrome (Otto et al., 1984, Plant Cell Physiol. 25:1579-1584; Lissemore et al., 1988, Mol. Cell. Biol. 8:4840-4850; Kay et al. 1989, Plant Cell 1:357-360), protochlorophyllide reductase (Mosinger et al., 1985, Eur. J. Biochem. 147:137-142) and an unidentified mRNA found in Lemna (Okubara et al., 1988, Plant Mol. Biol. 11:673-681). As shown for phytochrome (Lissemore et al., 1988; Kay et al., 1989) and protochlorophyllide reductase genes (Mosinger et al., 1985), the repression of AS1 mRNA accumulation in the light is a phytochrome-mediated response. We have determined that the dark-induced (or light-repressed) expression of AS1 reflects a transcriptional response as has also been shown for phytochrome (Lissemore and Quail, 1988; Kay et al., 1989) and protochlorophyllide reductase (Mosinger et al., 1985). The rapid changes in levels of AS1 mRNA suggest that a post-transcriptional response (e.g., mRNA stability) may also be involved as has been shown for another dark-induced gene of unknown function (Okubara et al., 1988). In direct contrast to the dark-induced accumulation of AS1 mRNA in leaves, the mRNA for the chloroplast form of glutamine synthetase (GS2) accumulates in the light in a phytochrome-mediated response (Tingey et al., 1988, J. Biol. Chem. 263:9651-9657). Parallel molecular studies on the mechanisms for dark-induced accumulation of AS1 mRNA and light-induced accumulation of GS2 mRNA will uncover how two genes encoding nitrogen metabolic enzymes along a common pathway are regulated by light via phytochrome in opposite fashions.

Previous biochemical studies have revealed high levels of AS activity in two developmental contexts where large amounts of asparagine are synthesized for nitrogen transport: in cotyledons of germinating seedlings (Capdevila et al., 1977, Plant Physiol. 59:268-273; Dilworth et al., 1978, Plant Physiol. 61:698-702; Kern et al., 1978, plant Physiol. 62:815-891) and in nitrogen-fixing root nodules (Scott et al., 1976, Nature 263:703-705; Reynolds et al., 1982, Physiol. Plant 55:255-260). Previous studies also showed that actinomycin D treatment abolished the induction of AS activity in cotyledons of germinating cotton seedlings, indicating that AS expression in cotyledons is regulated at the transcriptional level (Capdevila et al., 1977; Dilworth et al., 1978. Consistent with those findings, we have shown that the accumulation of both AS1 and AS2 mRNAs are induced to high levels in cotyledons of germinating seedlings. Comparative studies of AS mRNAs and GS mRNAs in this context show that the steady-state levels of mRNA for cytosolic GS accumulate earlier than those of both AS mRNAs in cotyledons of germinating seedlings. These results suggest that glutamine synthesized by GS may act as a metabolic signal to induce AS gene expression in this developmental context. The mRNAs of AS1 and AS2 also accumulate to very high levels in root nodules of peas in a parallel fashion with cytosolic GS mRNA. The accumulation of AS1 and AS2 mRNA in nitrogen-fixing nodules may be the result of factors produced by the process of nodulation or/and by metabolic factor(s) such as ammonia or glutamine production in nodules.

Southern blot analysis of genomic DNA reveals that the gene family for AS in peas is composed of at least two genes, AS1 and AS2, which encode homologous but distinct gene products. Expression studies show that AS1 and AS2 genes share some similarities in expression patterns (e.g. induced accumulation of mRNA in cotyledons and nodules); however, they have distinct organ-specific patterns of expression. AS1 mRNA accumulates to higher levels in leaves compared to AS2, while AS2 mRNA accumulates to higher levels in roots than AS1. In this respect, the AS gene family resembles the GS gene family where members of a gene family may be differentially regulated by distinct factors which modulate expression of individual genes in specific contexts during development.

7. EXAMPLE: THE AS PROMOTER

The subsections below describe the AS promoter sequence and its induction by dark.

7.1. DARK-INDUCED ACCUMULATION OF AS mRNA OCCURS IN ALL ORGANS TESTED

The results described in Section 6, supra, demonstrate that the AS1 mRNA accumulates within 6 hours of dark-treatment and that the photoreceptor phytochrome mediates the dark-induced accumulation of AS1 mRNA. In the experiments described herein, we have examined the effect of dark-treatment on AS gene expression in other plant organs. The steady-state levels of AS1 and AS2 mRNA were detected by gene specific Northern blot analysis in leaves, stems, and roots of light-grown (FIG. 7, lanes 1, 3, 5) or dark-adapted (FIG. 7, lanes 2, 4, 6) pea plants. These results show that AS1 mRNA accumulates to very high levels in all organs of dark-treated plants. The accumulation of AS2 mRNA is also induced by dark-treatment in leaves and stems. However, the steady-state levels of AS2 mRNA in dark-adapted plants was lower than that of AS1 mRNA. Interestingly, the steady-state levels of AS2 mRNA do not increase in roots after dark-treatment. This may be due to higher steady-state levels of AS2 mRNA in light-grown roots compared to AS1.

7.2. THE DARK-INDUCED EXPRESSION OF AS1 GENE IS NOT REGULATED BY CIRCADIAN RHYTHM

Figure 8A:
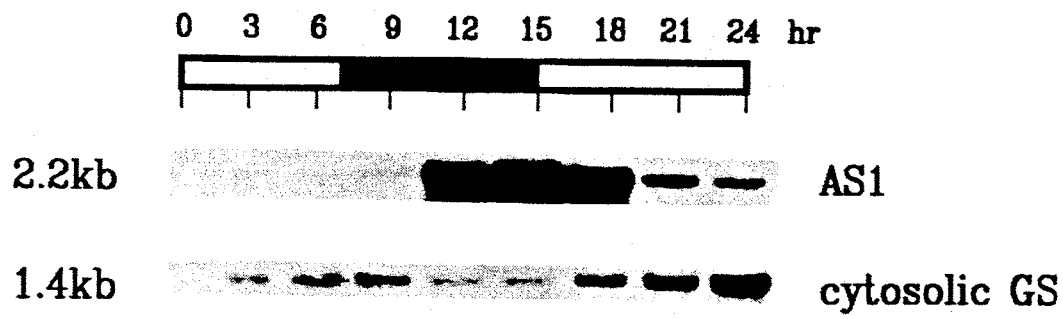
Figure 8B:
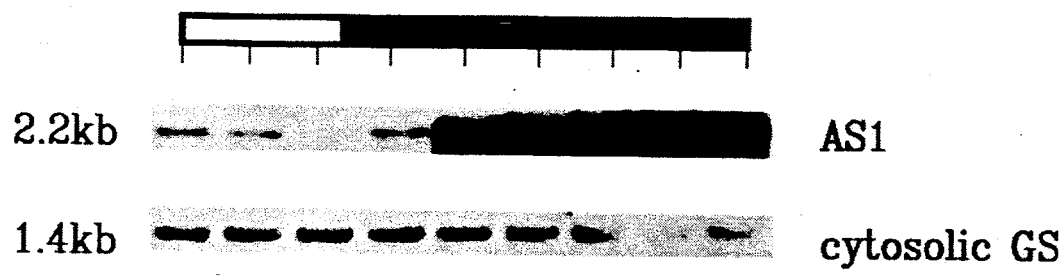
Figure 8C:
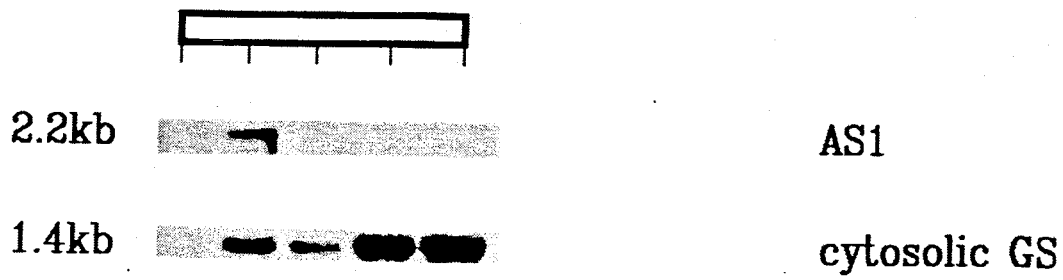

Gene-specific Northern blot analysis on the total RNA isolated from leaves collected at different time points of a day with variant light/dark conditions were performed to examine whether circadian rhythm is involved in the regulation of AS1 gene expression (FIG. 8). FIG. 8A shows that the accumulation of AS1 mRNA can be detected within 5 hours in the darkness and reach peak levels after 8 hours in the darkness. The decrease of AS1 mRNA level can be detected within 3 hours in the light; after 6 hours in the light the AS1 mRNA almost reach the minimum level. In the condition of extended darkness, the AS1 mRNA levels were kept at a very high level (FIG. 8B). On the contrary, the extended light condition maintained the AS1 mRNA at basal low levels (FIG. 8C). These results reveal that circadian rhythm is not involved in the dark-induced expression of AS1 gene. As a control, the mRNA levels of cytosolic GS were detected.

7.3. THE DARK-INDUCED EXPRESSION OF AS GENES IN PEA LEAVES IS REGULATED AT THE LEVEL OF TRANSCRIPTION

Nuclear run-on assays were performed to determine whether dark-treatment increases the transcription rate of AS gene (FIG. 9). These run-on experiments demonstrate that the AS1 gene is transcribed at a high level in leaves of dark-grown peas (FIG. 9, panel 2D). For AS2, the transcription rate is significantly lower than that of AS1 in leaves of dark-grown peas (FIG. 9, panel 3D). As a control, the transcription of genes for chloroplast GS and cytosolic GS were also monitored (FIG. 9, panels 4, 5). After the pea plants were transferred to continuous light for 6 hours, the transcription rate of AS1 decreases dramatically and the transcription rate of AS2 is also lower in light grown leaves (FIG. 9, panels 2L, 3L). These results show that while both AS1 and AS2 genes are preferentially transcribed in the dark, the AS1 gene is transcribed at a higher level in dark-grown leaves. As a control, we demonstrated that the transcription rate of the nuclear gene for chloroplast GS increases after light-treatment, and the transcription rate of cytosolic GS is relatively unchanged in different dark/light conditions (FIG. 9, panels 4, 5). These results demonstrate that the dark-induced expression of both AS1 and AS2 genes is regulated at the transcriptional level.

7.4. THE 569 BASE PAIR FRAGMENT OF THE AS1 PROMOTER IS SUFFICIENT TO DRIVE GUS EXPRESSION IN TRANSGENIC PLANTS

FIG. 10 shows the AS1 promoter sequence with nucleotides numbered relative to the transcription start site. Four AS1 promoter-GUS transcriptional fusions containing different lengths of the AS1 promoter fused to GUS were made and introduced into tobacco plants (FIG. 11). GUS activity was analyzed in leaves of dark-adapted transgenic plants to determine the expression of the GUS gene driven by AS1 promoter. GUS activity was detected in leaves of five dark-grown transgenic tobacco plants. Among them, two contain the pBI-AS1001 construct, and three contain the pBI-AS1003 construct (FIG. 11). Four out of these five transgenic tobacco express GUS specifically in phloem cells. We have also found a phloem-specific expression pattern of cytosolic GS (Jefferson, 1987, Plant Mol. Bio. Reporter 5:387–405). These results strongly suggest that the AS1 gene is specifically expressed in phloem cells, and that the 569 base-pair fragment containing nucleotides −558 to +11 of the AS1 promoter is sufficient to drive the phloem-specific expression of GUS in leaves of dark-grown plants.

7.5. AS1 AND AS2 GENES CONTAIN CONSERVED SEQUENCE IN THEIR PROMOTERS

The promoter sequence of the AS2 gene was determined by sequencing serial deletion clones of gAS2a fragment (FIG. 12). Since the sequence from nucleotides −558 to +11 of AS1 gene is sufficient to drive the phloem-specific expression in the dark (FIG. 11), this portion of the AS1 promoter was compared with the entire AS2 promoter sequence shown in FIG. 12. FIG. 13 shows sequences conserved between AS1 and AS2 promoters as determined by the computer program DNASIS.

8. DEPOSIT OF MICROORGANISMS

The following microorganisms have been deposited with the Agricultural Research Culture Collection, Northern Regional Research Center (NRRL) and have been assigned the following accession numbers:

| Microorganism | Plasmid | Accession No. |
| --- | --- | --- |
| Escherichia coli XL1 | pTZ18U/cAS1 | B-18487 |
| Escherichia coli XL1 | pTZ19U/cAS201 | B-18486 |
| Escherichia coli XL1 | pTZ18U/gAS1.a | B-18492 |
| Escherichia coli XL1 | pTZ18U/gAS2.a | B-18493 |
| Escherichia coli XL1 | pTZ19U/cAS801 | B-18649 |

The present invention is not to be limited in scope by the microorganisms deposited since the deposited embodiments are intended as illustrations of single aspects of the invention and any microorganisms which are functionally equivalent are within the scope of the invention. Indeed, various modifications of the invention in addition to those shown and described herein will become apparent to those skilled in the art from the foregoing description and accompanying drawings. Such modifications are intended to fall within the scope of the appended claims.

It is also to be understood that all base pair sizes given for nucleotides are approximate and are used for purposes of description.

What is claimed is:

1. An isolated nucleotide sequence encoding plant asparagine synthetase which is capable of selectively hybridizing to the nucleotide sequence of FIG. 2a or 2b, or which encodes substantially the same amino acid sequence of FIG. 2a or 2b.

2. A substantially pure nucleotide sequence encoding plant asparagine synthetase comprising the nucleotide sequence substantially as depicted in FIG. 2A from nucleotide residue number 94 to nucleotide residue number 1851.

3. A substantially pure nucleotide sequence encoding plant asparagine synthetase comprising the nucleotide sequence substantially as depicted in FIG. 2B from nucleotide residue number 102 to nucleotide residue number 1850.

4. A recombinant DNA molecule containing a nucleotide sequence encoding plant asparagine synthetase, which is capable of selectively hybridizing to the nucleotide sequence of FIG. 2a or 2b, or which encodes substantially the same amino acid sequence of FIG. 2a or 2b.

5. The recombinant DNA molecule according to claim 4 in which the nucleotide sequence encoding plant asparagine synthetase comprises the nucleotide sequence substantially as depicted in FIG. 2A from nucleotide residue number 94 to 1851.

6. The recombinant DNA molecule according to claim 4 in which the nucleotide sequence encoding plant asparagine synthetase comprises the nucleotide sequence substantially as depicted in FIG. 2B from nucleotide residue number 102 to 1850.

7. Recombinant plasmid pTZ18U/cAS1.

8. Recombinant plasmid pTZ19U/cAS201.

9. Recombinant plasmid pTZ18U/gAS1.a.

10. Recombinant plasmid pTZ18U/gAS2.a.

11. Recombinant plasmid pTZ19U/cAS801.

12. A cultured cell containing a recombinant nucleotide sequence encoding plant asparagine synthetase which is capable of selectively hybridizing to the nucleotide sequence of FIG. 2a or 2b, or which encodes substantially the same amino acid sequence of FIG. 2a or 2b.

13. The cultured cell according to claim 12 in which the nucleotide sequence encoding plant asparagine synthetase comprises the nucleotide sequence substantially as depicted in FIG. 2A from nucleotide residue number 94 to 1851.

14. The cultured cell according to claim 12 in which the nucleotide sequence encoding plant asparagine synthetase comprises the nucleotide sequence substantially as depicted in FIG. 2B from nucleotide residue number 102 to 1850.

15. Escherichia coli XL1 transformed with pTZ18U/cAS1 as deposited with the NRRL and assigned accession number B-18487.

16. Escherichia coli XL1 transformed with pTZ19U/cAS201 as deposited with the NRRL and assigned accession number B-18486.

17. Escherichia coli XL1 transformed with pTZ19U/cAS801 as deposited with the NRRL and assigned accession number B-18649.

18. A cultured cell containing a recombinant genomic nucleotide sequence encoding exons for plant asparagine synthetase, which is capable of selectively hybridizing to the nucleotide sequence of FIG. 2a or 2b, or which encodes substantially the same amino acid sequence of FIG. 2a or 2b.

19. A cultured cell containing a recombinant genomic nucleotide sequence for asparagine synthetase as contained in pTZ18U/gAS1.a.

20. A cultured cell containing a recombinant genomic nucleotide sequence for asparagine synthetase as contained in a pTZ18U/gAS2.a.

21. Escherichia coli XL1 transformed with pTZ18U/gAS1.a as deposited with the NRRL and assigned accession number B-18492.

22. Escherichia coli XL1 transformed with pTZ18U/gAS2.a as deposited with the NRRL and assigned accession number B-18493.

23. A cultured cell containing a recombinant nucleotide sequence encoding plant asparagine synthetase controlled by a second nucleotide sequence that regulates gene expression in the cultured cell, so that the cultured cell produces plant asparagine synthetase, in which the recombinant nucleotide sequence is capable of selectively hybridizing to the nucleotide sequence of FIG. 2a or 2b, or encodes substantially the same amino acid sequence of FIG. 2a or 2b.

24. The cultured cell according to claim 23 in which the nucleotide sequence encoding plant asparagine synthetase comprises the nucleotide sequence substantially as depicted in FIG. 2A from nucleotide residue number 94 to 1851.

25. The cultured cell according to claim 23 in which the nucleotide sequence encoding plant asparagine synthetase comprises the nucleotide sequence substantially as depicted in FIG. 2B from nucleotide residue number 102 to 1850.

26. A substantially pure plant asparagine synthetase promoter comprising the nucleotide sequence substantially as depicted in FIG. 10 from nucleotide residue number −558 to +11.

27. A substantially pure plant asparagine synthetase promoter comprising the nucleotide sequence substantially as depicted in FIG. 10 from nucleotide residue number −2376 to +11.

28. A substantially pure plant asparagine synthetase promoter comprising the nucleotide sequence substantially as depicted in FIG. 12 from nucleotide residue number 1 to 1031.

29. A recombinant DNA molecule containing an inducible plant asparagine synthetase promoter which is capable of selectively hybridizing to the nucleotide sequence of FIG. 10 or FIG. 12.

30. A recombinant DNA molecule containing a plant asparagine synthetase promoter which is inducible by dark and is capable of selectively hybridizing to the nucleotide sequence of FIG. 10 or FIG. 12.

31. The recombinant DNA molecule according to claim 29 in which the plant asparagine synthetase promoter comprises the nucleotide sequence substantially as depicted in FIG. 10 from nucleotide residue number −558 to +11.

32. The recombinant DNA molecule according to claim 29 in which the plant asparagine synthetase promoter comprises the nucleotide sequence substantially as depicted in FIG. 10 from nucleotide residue number −2376 to +11.

33. The recombinant DNA molecule according to claim 29 in which the plant asparagine synthetase promoter comprises the nucleotide sequence substantially as depicted in FIG. 12 from nucleotide residue number 1 to 1031.

* * * * *